(12) United States Patent
Patel

(10) Patent No.: US 12,257,124 B1
(45) Date of Patent: Mar. 25, 2025

(54) DENTAL ROBOT

(71) Applicant: Amrish Patel, Virginia Beach, VA (US)

(72) Inventor: Amrish Patel, Virginia Beach, VA (US)

(*) Notice: Subject to any disclaimer, the term of this patent is extended or adjusted under 35 U.S.C. 154(b) by 0 days.

(21) Appl. No.: 18/904,979

(22) Filed: Oct. 2, 2024

Related U.S. Application Data

(60) Provisional application No. 63/641,326, filed on May 1, 2024.

(51) Int. Cl.
| | |
|---|---|
| *A61C 7/00* | (2006.01) |
| *A61B 34/30* | (2016.01) |
| *A61C 9/00* | (2006.01) |
| *G06T 7/00* | (2017.01) |

(52) U.S. Cl.
CPC .............. *A61C 7/002* (2013.01); *A61B 34/30* (2016.02); *A61C 9/0053* (2013.01); *G06T 7/0012* (2013.01); *G06T 2207/30036* (2013.01)

(58) Field of Classification Search
CPC ....... A61C 7/002; A61C 9/0053; A61B 34/30; G06T 7/0012; G06T 2207/30036
See application file for complete search history.

(56) References Cited

U.S. PATENT DOCUMENTS

| | | |
|---|---|---|
| 9,861,457 B2 | 1/2018 | Fisker et al. |
| 10,716,630 B2 | 7/2020 | Krebs et al. |
| 10,959,814 B2 | 3/2021 | Suttin et al. |
| 11,185,395 B2 | 11/2021 | Barak et al. |
| 11,273,091 B2 | 3/2022 | Zhang et al. |
| 11,864,727 B2 | 1/2024 | Ciriello et al. |

(Continued)

FOREIGN PATENT DOCUMENTS

| | | |
|---|---|---|
| CN | 106725914 A | 5/2017 |
| CN | 108969281 A | 12/2018 |

(Continued)

OTHER PUBLICATIONS

Ahmad, et al., Dental Robotics: A Disruptive Technology, Sensors 2021, 21, 3308, 15 pages. https://doi.org/10.3390/s21103308.

(Continued)

*Primary Examiner* — Ping Y Hsieh
*Assistant Examiner* — Jose M Torres

(57) ABSTRACT

Herein disclosed are robotic dentistry methods comprising tooth extraction and crown preparation. Robotic tooth extraction may comprise determining if the correct tooth is targeted, based on a scanned image; determining a decay state of the tooth based on the scanned image; selecting an extraction technique determined as a function of the decay state; and extracting the tooth using the selected extraction technique. Robotic crown preparation may comprise receiving an initial reduction plan to reduce a tooth; presenting, to a dentist for approval, the initial reduction plan for approval; upon approval, reducing the tooth according to the approved initial reduction plan; upon rejection, modifying the initial reduction plan based on dentist input; receiving the modified reduction plan to reduce the tooth; presenting, to a dentist for approval, the modified reduction plan for approval; and upon approval of the modified reduction plan, reducing the tooth according to the approved modified reduction plan.

20 Claims, 15 Drawing Sheets

(56) References Cited

U.S. PATENT DOCUMENTS

| | | | |
|---|---|---|---|
| 12,016,653 | B2 | 6/2024 | Ciriello et al. |
| 12,029,619 | B2 | 7/2024 | Ciriello et al. |
| 12,036,093 | B2 | 7/2024 | Roschin et al. |
| 12,079,311 | B2 | 9/2024 | Esteva et al. |
| 2011/0070554 | A1 | 3/2011 | Kopelman et al. |
| 2015/0056576 | A1 | 2/2015 | Nikolskiy et al. |
| 2020/0390518 | A1 | 12/2020 | Ciriello et al. |
| 2022/0142736 | A1 | 5/2022 | Kim |
| 2022/0304646 | A1* | 9/2022 | Tuzoff .................. A61B 6/5217 |
| 2022/0346924 | A1 | 11/2022 | Koo et al. |
| 2022/0361996 | A1 | 11/2022 | Raby et al. |
| 2023/0158716 | A1 | 5/2023 | Nishimuta et al. |
| 2023/0190182 | A1* | 6/2023 | Abramoff ............ A61B 5/7264 382/131 |

FOREIGN PATENT DOCUMENTS

| | | |
|---|---|---|
| WO | 2012/010916 A1 | 1/2012 |
| WO | 2018/022752 A1 | 2/2018 |
| WO | 2024/077141 A1 | 4/2024 |

OTHER PUBLICATIONS

Automatic Addison, The Ultimate Guide to Inverse Kinematics for 6DOF Robot Arms, Oct. 23, 2020, https://automaticaddison.com/the-ultimate-guide-to-inverse-kinematics-for-6dof-robot-arms/, downloaded Jul. 13, 2024, 33 pages.

Ayhan, et al., A novel deep learning-based perspective for tooth numbering and caries detection, Nov. 15, 2023, 17 pages, https://doi.org/10.1007/s00784-024-05566-w.

Carneiro, et al., Deep Learning to Detect and Classify Teeth, Dental Caries and Restorations: A Systematic Mapping, Jul. 13, 2023, 36 pages, https://doi.org/10.21203/rs.3.rs-3150325/v1.

Casalegno, et al., Caries Detection with Near-Infrared Transillumination Using Deep Learning, Journal of Dental Research, 2019, vol. 98 (11) 1227-1233.

Chen, et al., A deep learning approach to automatic teeth detection and numbering based on object detection in dental periapical films, Scientific Reports, Oct. 24, 2018, 11 pages, https://doi.org/10.1038/s41598-019-40414-y.

Dibart, et al., Robot assisted implant surgery: Hype or hope?, Elsevier Masson SAS, Apr. 13, 2023, 3 pages.

Duong, et al., Proof-of-Concept Study on an Automatic Computational System in Detecting and Classifying Occlusal Caries Lesions from Smartphone Color Images of Unrestored Extracted Teeth, Diagnostics 2021, 11, 1136, https://doi.org/10.3390/diagnostics11071136.

Emu, et al., Development of a Feeding Assistive Robot Using a Six Degree of Freedom Robotic Arm, downloaded Sep. 20, 2023, 5 pages, arXiv:2309.11594v1.

Glodny, et al., The occurrence of dental caries is associated with atherosclerosis, Clinics, 2013; 68(7): 946-953.

Guibas, et al., An Empirical Comparison of Techniques for Updating Delaunay Triangulations, SCG'04, Jun. 8-11, 2004, Brooklyn, New York, USA, 10 pages.

Guist, et al., Safe & Accurate at Speed with Tendons: A Robot Arm for Exploring Dynamic Motion, 5 pages, downloaded Jul. 2, 2024, arXiv:2307.02654v4.

Haghanifar, Automated Teeth Extraction and Dental Caries Detection in Panoramic X-ray, University of Saskatchewan, Feb. 2022, 89 pages.

Hu, Modelling and Control System of a Six Degree-of-freedom Robotic Manipulator for Shipbuilding Welding, Jul. 2022, 71 pages.

Kothari, Six Degree Robotic Arm With Mimicking Mechanism, University of Michigan, 2020, 66 pages.

Kumar, et al., Descriptive analysis of dental X-ray images using various practical methods: A review, PeerJ Computer Science, Apr. 5, 2021, 41 pages.

Li, et al., Clinical application of robots in dentistry: A scoping review, Journal of Prosthodontic Research, 2024; 68(2):193-205.

Lian, et al., Deep Learning for Caries Detection and Classification, Diagnostics 2021, 11, 1672, 11 pages, https://doi.org/10.3390/diagnostics11091672.

Liu, et al., Robotics in Dentistry: A Narrative Review, Narrative Review. Dent. J. 2023, 11, 62, https://doi.org/10.3390/dj11030062.

Lunia, Inverse Kinematics—Modeling, Motion Planning, and Control of Manipulators and Mobile Robots, Clemson University, downloaded Jul. 13, 2024, https://opentextbooks.clemson.edu/wangrobotics/chapter/inverse-kinematics/.

Massachusetts Institute of Technology, 6.886 Delaunay Triangulation, 2018, 69 pages.

Morton, et al., Current state of CAD/CAM technology in implant dentistry, International Dentistry—African Edition, vol. 11, No. 4 Aug./Sep. 2021, 11 pages.

Neto, et al., Influence of Cavity Geometry on the Fracture Strength of Dental Restorations: Finite Element Study, Appl. Sci. 2021, 11, 4218, https://doi.org/10.3390/app11094218.

Omron, Technical Explanation for Servomotors and Servo Drives, 19 pages, https://www.ia.omron.com/data_pdf/guide/14/servo_tg_e_1_1.pdf. (Oct. 22, 2024).

Rashid, et al., A hybrid mask RCNN-based tool to localize dental cavities from real-time mixed photographic images, PeerJ Computer Science, Sep. 21, 2021, 24 pages.

Shafi, et al., A Comprehensive Review of Recent Advances in Artificial Intelligence for Dentistry E-Health, Diagnostics 2023, 13, 2196, https://doi.org/10.3390/diagnostics13132196.

Sin, et al., Development of a Real-Time 6-DOF Motion-Tracking System for Robotic Computer-Assisted Implant Surgery, Sensors 2023, 23, 2450, https://doi.org/10.3390/s23052450.

Tang, et al., High-precision all-in-one dual robotic arm strategy in oral implant surgery, Logistics Engineering College, Shanghai, China, Mar. 21, 2024, 10 pages.

Tao, et al., A Compact Asymmetrical Manipulator for Robotic Dentistry, Proceedings of 9th IEEE International Conference on CYBER Technology in Automation, Control, and Intelligent Systems Jul. 29-Aug. 2, 2019, Suzhou, China, 5 pages.

Tareq, et al., Visual Diagnostics of Dental Caries through Deep Learning of Non-Standardised Photographs Using a Hybrid YOLO Ensemble and Transfer Learning Model, Int. J. Environ. Res. Public Health 2023, 20, 5351, https://doi.rg/10.3390/ijerph20075351.

Tung, et al., Development of a prototype 6 degree of freedom robot arm, Results in Engineering 18, Jan. 25, 2023, 12 pages, https://doi.org/10.1016/j.rineng.2023.101049.

Tuzoff, Tooth detection and numbering in panoramic radiographs using convolutional neural networks, Dentomaxi/lofacia/ Radiology, vol. 48, Issue 4, May 1, 2019, 23 pages, https://doi.org/l0.1259/dmfr.20180051.

University of Illinois Urbana-Champaign, Introduction to Robotics Lecture 11: Inverse Kinematics, Oct. 2021, 15 pages.

Van Riet, et al., Robot technology in dentistry, part two of asystematic review: an overview of initiatives, Dental Materials 37 (2021), 1227-1236, 10 pages.

Xu, et al., Accuracy and efficiency of robotic dental implant surgery with different human-robot interactions: An in vitro study, Journal of Dentistry 137 (2023), 9 pages.

Yan, et al., Optics-guided Robotic System for Dental Implant Surgery, Chinese Journal of Mechanical Engineering (2022) 35:55, https://doi.org/10.1186/s10033-022-00732-1.

Zhang, et al., Design and analysis of a six degrees of freedom serial-parallel robotic mechanism with multi-degree of freedom legs, International Journal of Advanced Robotic Systems Nov.-Dec. 2018: 1-14.

Zhao, et al., Inverse kinematics solution and control method of 6-degree-of-freedom manipulator based on deep reinforcement learning, Scientific Reports (2024), 14:12467, https://doi.org/10.1038/s41598-024-62948-6.

Zhou, et al., Design and Control of a Tendon-Driven Robotic Finger Based on Grasping Task Analysis, Biomimetics 2024, 9, 370, https://doi.org/10.3390/biomimetics9060370.

* cited by examiner

DENTAL ROBOT

CROSS-REFERENCE TO RELATED APPLICATIONS

This application claims the benefit of U.S. Provisional Patent Application No. 63/641,326, titled "TOOTH EXTRACTION AND CROWN PREPARATION ROBOT," filed by Amrish Patel on May 1, 2024, and this application incorporates the entire contents of the above-referenced application herein by reference.

TECHNICAL FIELD

This disclosure relates generally to robotic dentistry.

BACKGROUND

The field of robotic dentistry has seen significant advancements in recent years, with several solutions emerging to assist dentists in tooth extraction and preparing teeth for crowns. Some such solutions may use automated dental robots with computer-aided design (CAD) software to create a digital model of the tooth and surrounding anatomy. The robot may then use this digital model to identify the tooth for extraction or precisely prepare the tooth for a crown, utilizing a combination of drilling and milling techniques. Key terms in this process include "tooth reduction," which refers to the process of removing a portion of the tooth structure to accommodate the crown, and "CAD/CAM" (computer-aided design/computer-aided manufacturing), which describes the integration of digital design and manufacturing processes.

Other solutions have also emerged to automate aspects of robotic dentistry, such as using a robotic arm to precisely place restorations, such as crowns or inlays, onto prepared teeth. Some such systems use a robot arm to perform tasks such as drilling and milling teeth for crown preparation. These systems often rely on pre-programmed software algorithms to guide robotic dentistry processes.

Despite these advancements, existing solutions in robotic dentistry are not without their limitations. One significant deficiency is the lack of integration between human dental expertise and the automated tooth extraction and tooth reduction processes. In existing systems, the dentist may be involved in the initial design phase but has limited ability to confirm or adjust the tooth extraction or the tooth reduction plan before the robot performs the procedure. This can lead to issues such as misidentification in tooth extraction or inaccuracies in tooth reduction, which can result in compromised patient outcomes such as wrong tooth extraction or suboptimal crown fit.

It is therefore an objective of the present application to integrate the human dentist more thoroughly into a confirmation and adjustment loop of tooth extraction and tooth reduction planning. Integrating the human dentist more thoroughly into this planning confirmation and adjustment loop will allow for more precise and effective tooth identification and preparation processes that leverage the strengths of both human expertise and automated technology. This will enable dentists to work in conjunction with the dental robot to ensure optimal results for patients, while also minimizing the potential for errors or inaccuracies.

SUMMARY

Herein disclosed is tooth extraction comprising receiving a scanned image of a tooth and a surrounding area, using at least one processor, presenting the scanned image of the tooth to a dentist, using the at least one processor and a user interface, upon receiving confirmation the correct tooth is targeted: severing a periodontal ligament and luxating the tooth, using the at least one processor and an elevator/luxator, determining if the tooth is decayed based on analysis of the scanned image of the tooth, using the at least one processor; in response to determining the tooth is decayed, grabbing the neck of the tooth, using the at least one processor and forceps, and in response to determining the tooth is not decayed, grabbing a firm surface of the tooth, using the at least one processor and the forceps, and extracting the tooth, using the at least one processor and the forceps.

Herein disclosed is crown preparation comprising receiving an initial reduction plan to reduce a tooth, using at least one processor; presenting, to a dentist, the initial reduction plan for approval; upon approval of the initial reduction plan, reducing the tooth according to the approved initial reduction plan, using a reducing tool and the at least one processor; upon rejection, by the dentist, of the initial reduction plan, modifying the initial reduction plan based on input from the dentist; receiving the modified reduction plan to reduce the tooth, using the at least one processor; presenting, to a dentist, the modified reduction plan for approval; upon approval of the modified reduction plan, reducing the tooth according to the approved modified reduction plan, using the reducing tool and the at least one processor. Various implementations may advantageously integrate the expertise of a human dentist into confirming and adjusting reduction plans for crown preparation.

The details of various implementations are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION

Figure 1:
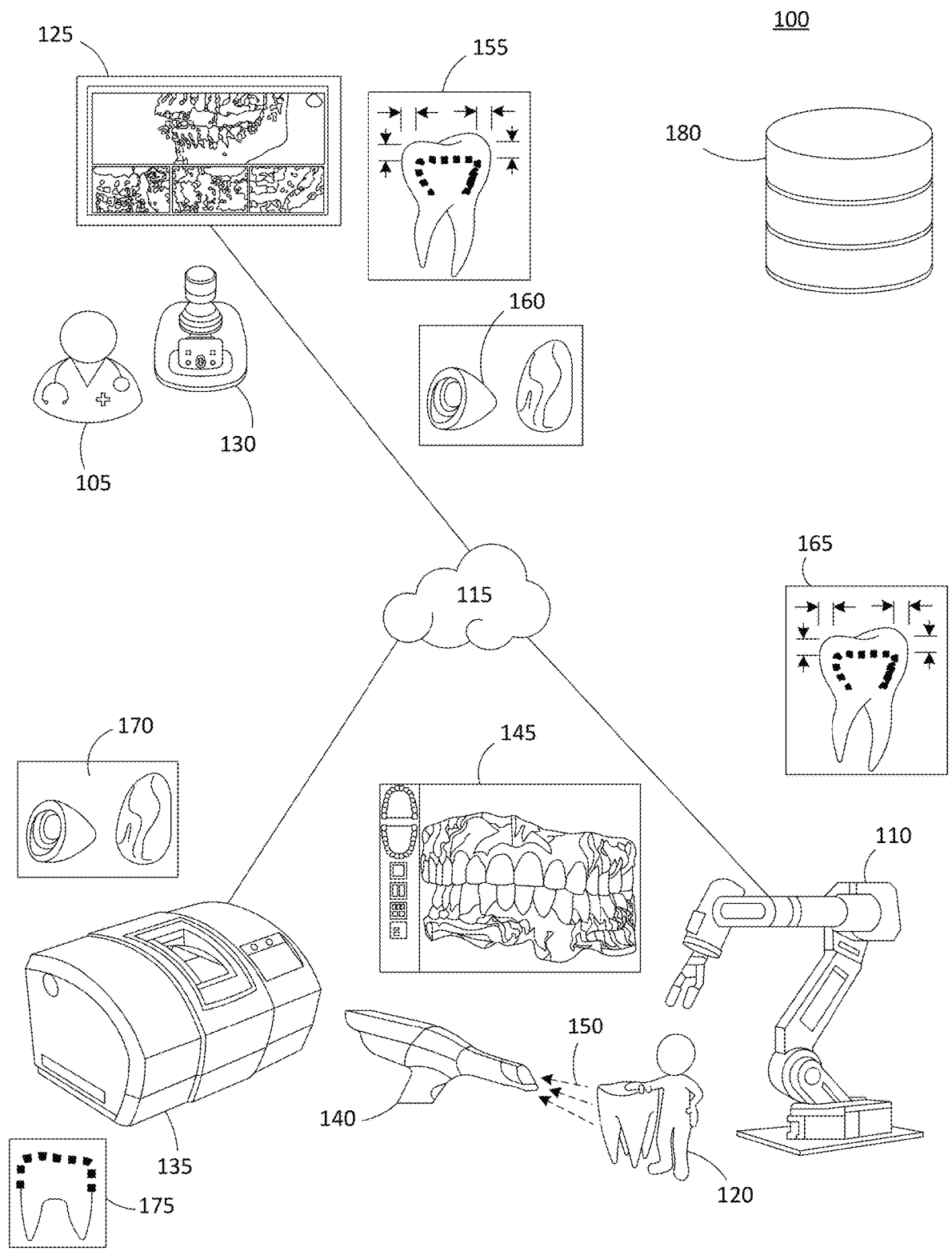
FIG. 1 depicts an illustrative operational scenario wherein a dentist uses an exemplary robotic dentistry system configured to integrate the expertise of a human dentist into confirming and adjusting reduction plans for crown preparation and extraction plans for tooth extraction.

FIG. 1 depicts an illustrative operational scenario wherein a dentist uses an exemplary robotic dentistry system configured to integrate the expertise of a human dentist into confirming and adjusting reduction plans for crown preparation and extraction plans for tooth extraction.

In FIG. 1, the exemplary system 100 enables the dentist 105 to use the dental robot 110 via the network cloud 115 to treat the patient 120. In the depicted implementation the system 100 is a robotic dentistry system. In the depicted implementation the dentist 105 uses the user interface display 125 to interact with and control the dental robot 110 and the dental mill 135. The user interface display 125 may comprise a touch screen. In the depicted implementation the dentist 105 may use the user interface control 130 to interact with software in a computer connected to the network cloud 115. The user interface control may comprise a mouse or joystick. In the depicted implementation the dentist 105 may use the dental robot 110 in an exemplary crown preparation mode to prepare a tooth to receive a crown. The dental mill 135 may be used to fabricate a crown to fit a tooth prepared by dentist using the dental robot 110. In the depicted implementation the dentist 105 may use the dental robot 110 in an exemplary tooth extraction mode to prepare a tooth for extraction and extract the tooth.

In an exemplary crown preparation mode, the dentist 105 or the dental robot 110 may use the optical scanner 140 to generate the three-dimensional map 145 of the patient 120 teeth from the optical scan 150. The dentist 105 may design the initial reduction plan 155 via the user interface display 125 and the user interface control 130. The dental robot 110 may design the initial reduction plan 155 based on the optical scan 150. In any case, in the depicted implementation, the dental robot 110 receives the initial reduction plan 155. The dental robot 110 presents the initial reduction plan 155 to the dentist 105 for approval via the user interface display 125. In the depicted implementation, the system 100 may use the dental mill 135 and the initial fabrication plan 160 for fabricating a crown to fit the prepared tooth. The initial fabrication plan 160 may be designed by the dentist 105. Upon receiving dentist 105 approval of the initial reduction plan 155 via the user interface display 125, the dental robot 110 reduces the tooth according to the approved initial reduction plan 165, using a reducing tool configured in the dental robot 110. The reducing tool may be an ablation tool. Upon receiving rejection of the initial reduction plan 155 by the dentist 105 via the user interface display 125, the dental robot 110 may modify the initial reduction plan 155 based on input from the dentist 105 via the user interface display 125. In the depicted implementation, the dental robot 110 receives the modified reduction plan. The dental robot 110 presents the modified reduction plan to the dentist 105 for approval via the user interface display 125. Upon receiving dentist 105 approval of the modified reduction plan via the user interface display 125, the dental robot 110 reduces the tooth according to the approved modified reduction plan 165 using the reducing tool configured in the dental robot 110. Upon rejection of the modified reduction plan, the modified reduction plan may be iteratively modified until approval by the dentist 105, based on input from the dentist 105. The modified reduction plan may be presented to the dentist for approval, before reducing the tooth. In the depicted implementation, the dental robot 110 captures the three-dimensional optical scan 150 of the reduced tooth. In the depicted implementation, the dentist 105 uses the three-dimensional optical scan 150 of the reduced tooth and the reduced tooth three-dimensional digital map 175 to design the final crown fabrication plan 170. Upon approval by the dentist 105, the dentist 105 may send the final crown fabrication plan 170 to the dental mill 135, to use the most accurate representation of the reduced tooth to form a crown for the reduced tooth. In the depicted implementation, the dental mill 135 uses the final crown fabrication plan 170 to fabricate the crown. In the depicted implementation, the dental robot 110 places the crown on the prepared tooth. An X-ray may be captured to verify the fit of the fabricated crown to the tooth. In the depicted implementation, the dental robot 110 cements the fabricated crown to the reduced tooth. In the depicted implementation, the approved reduction plan 165 and the reduced tooth three-dimensional digital map 175 are stored in the procedure database 180.

In an exemplary tooth extraction mode, the dental robot 110 receives a scanned image of a tooth and a surrounding area in the mouth of the patient 120. The dental robot 110 may use the optical scanner 140 to capture the scanned image. In the depicted implementation, the dental robot 110 presents the scanned image of the tooth to the dentist 105, via the user interface display 125. Upon receiving confirmation from the dentist 105 via the user interface display 125 that the correct tooth is targeted for extraction, the dental robot 110 software locks in the targeted tooth for extraction.

In the depicted implementation, the dental robot 110 uses forceps to grab the neck of the tooth targeted for extraction. The dental robot 110 or the dentist 105 may determine if the tooth is decayed, based on analysis of the scanned image of the tooth. In the depicted implementation, in response to a determination the tooth is decayed, the dentist 105 may identify a firm surface on the tooth, using the user interface display 125. Then, the dental robot 110 may use the forceps to grab and extract the tooth by the firm surface identified by the dentist 105. In case the tooth targeted for extraction is completely decayed, the dentist 105 or the dental robot 110 may create an extraction plan for the completely decayed tooth, via the user interface display 125. The extraction plan for the completely decayed tooth created by the dentist 105 may comprise the dental robot 110 sectioning the roots of the decayed tooth using a surgical handpiece before elevating/luxating and then extracting the decayed tooth.

The dental robot 110 then begins severing a periodontal ligament and luxating the tooth, using an elevator/luxator configured in the dental robot 110. In the depicted implementation, the dental robot 110 extracts the tooth, using the forceps. The dental robot 110 may capture a scanned image of the area surrounding the extracted tooth, using the optical scanner 140. In the depicted implementation, the dental robot 110 determines if there is bleeding from the area surrounding the extracted tooth, based on analysis of the scanned image. In response to determining there is bleeding, the dental robot 110 may stop the bleeding, using a laser configured in the dental robot 110. In some cases, the dental robot may inject an anesthetic into the area surrounding the extracted tooth, using a syringe. The anesthetic may be Novocaine®.

Figure 2:
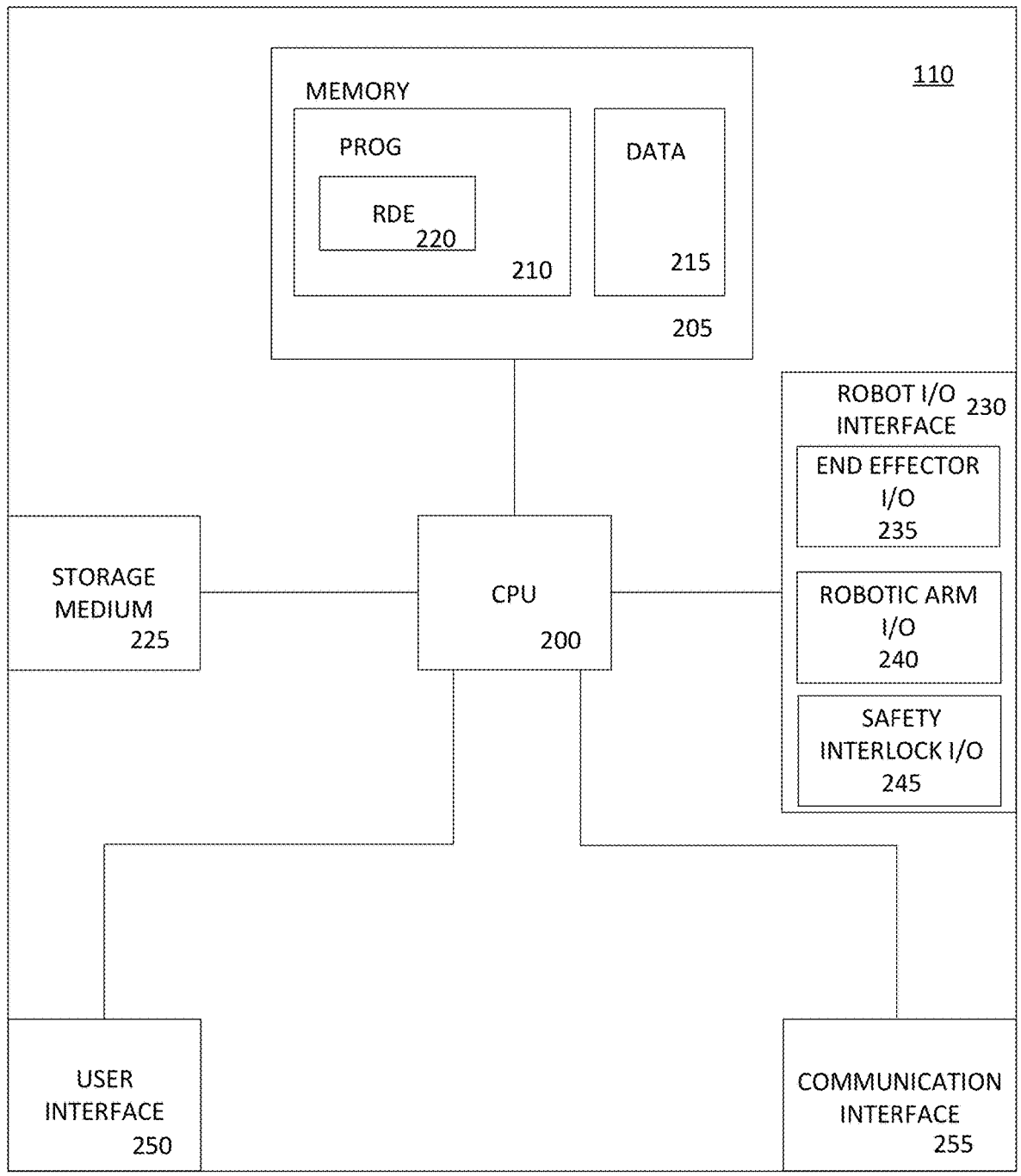
FIG. 2 depicts a schematic view of an exemplary controller for a dental robot configured to integrate the expertise of a human dentist into confirming and adjusting reduction plans for crown preparation and extraction plans for tooth extraction.

FIG. 2 depicts a schematic view of an exemplary controller for a dental robot configured to integrate the expertise of a human dentist into confirming and adjusting reduction plans for crown preparation and extraction plans for tooth extraction. In FIG. 2, the block diagram of the exemplary dental robot 110 controller includes the CPU (processor) 200 and the memory 205. In the depicted implementation, the processor 200 is in electrical communication with the memory 205. The processor 200 may be operably coupled with one or more memory 205 via a data bus or communication network. In the depicted implementation the memory 205 includes the program memory 210 and the data memory 215. The depicted program memory 210 includes processor-executable program instructions implementing the robotic dentistry engine (RDE) 220. In some embodiments, the illustrated program memory 210 may include processor-executable program instructions configured to implement an OS (Operating System). In various embodiments, the OS may include processor executable program instructions configured to implement various operations when executed by the processor 200. In some embodiments, the OS may be omitted. In some embodiments, the illustrated program memory 210 may include processor-executable program instructions configured to implement various Application Software. In various embodiments, the Application Software may include processor executable program instructions configured to implement various operations when executed by the processor 200. In some embodiments, the Application Software may be omitted. In the depicted embodiment, the processor 200 is communicatively and operably coupled with the storage medium 225. The storage medium 225 may be configured to implement various data storage and data retrieval operations for the processor 200 such as for example, read/write, read/only or non-volatile storage and retrieval.

In the depicted embodiment, the processor 200 is communicatively and operably coupled with the robot Input/Output (I/O) interface 230. In the depicted embodiment, the robot I/O interface 230 includes the end effector Input/Output (I/O) interface 235. In the depicted implementation, the end effector I/O interface 235 includes circuitry and programming configured to interface with, control and operate end effectors as described herein and as would be known to one of ordinary skill. In the depicted implementation, the end effector I/O interface 235 is a custom-designed subsystem configured to serve as a primary interface for end effectors operably coupled with the dental robot 110. In the depicted implementation, the end effector I/O interface 235 enables seamless communication and control between the robot's control system implemented by the RDE 220 and attached dental instruments or devices. In the depicted implementation, the end effector I/O interface 235 comprises digital I/O lines, analog inputs/outputs, and serial communication interfaces, configurable by the processor 200. The end effector I/O interface 235 may comprise 24-bit high-resolution digital I/O lines for controlling the end effector's actuators (e.g., grippers, suction cups, or other actuator types such as would be known by one of ordinary skill). The end effector I/O interface 235 may comprise 12-bit analog inputs (AINs) for monitoring the end effector's sensor data (e.g., force, torque, pressure or other sensor data types such as would be known by one of ordinary skill). The end effector I/O interface 235 may comprise 16-bit analog outputs (AOs) for driving the end effector's actuation devices (e.g., hydraulic or pneumatic pumps or other actuation device types such as would be known by one of ordinary skill). The end effector I/O interface 235 may comprise high-speed serial communication interfaces (e.g., RS422/485, I2C) for transmitting control signals and receiving feedback from the attached dental instruments. The end effector I/O interface 235 may comprise circuitry and/or programming configured to support a wide range of dental applications, such as would be known by one of ordinary skill including but not limited to tool calibration (e.g., interfacing real-time data for calibrating attached tools and ensuring accurate robotic movements) and end effector monitoring (e.g., continuously monitoring the end effector's performance, detecting faults or malfunctions that may affect the quality of the dental procedure).

In the depicted implementation, the robot I/O interface 230 includes the robotic arm Input/Output (I/O) interface 240. In the depicted implementation, the robotic arm I/O interface 240 includes circuitry and programming configured to drive motors, operate switches and receive information from sensors configured in robotic arms of the dental robot 110. In the depicted implementation, the robotic arm I/O interface 240 is a custom-designed subsystem integrated into the dental robot 110. In the depicted implementation, the robotic arm I/O interface 240 is configured to serve as an interface for the robotic arms of the dental robot 110, enabling seamless communication and control between the robot's control system implemented by the RDE 220 and the articulated limbs. In the depicted implementation, the robotic arm I/O interface 240 comprises digital I/O lines, analog inputs/outputs, and serial communication interfaces. For example, in the depicted implementation, the robotic arm I/O interface 240 may comprise 32-bit high-resolution digital I/O lines for controlling the arm's motors (e.g., joint actuators, gripper mechanisms or other motors of the dental robot 110). In the depicted implementation, the robotic arm I/O interface 240 may comprise 16-bit analog inputs (AINs) for monitoring the arm's sensor data (e.g., joint angles, velocities, accelerations or other sensor types as the person of ordinary skill might recognize). In the depicted implementation, the robotic arm I/O interface 240 may comprise 24-bit analog outputs (AOs) for driving the arm's actuation devices (e.g., hydraulic or pneumatic pumps, tendon-sheath or other robotic arm actuation types as the person of ordinary skill would recognize). In the depicted implementation, the robotic arm I/O interface 240 may comprise High-speed serial communication interfaces (e.g., RS422/485, I2C) for transmitting control signals and receiving feedback from the robotic arms. In the depicted implementation, the robotic arm I/O interface 240 is configured with circuitry and programming designed to support a wide range of dental applications, including but not limited to: arm position sensing comprising precise monitoring of the robotic arm's joint angles, allowing for accurate movements and precision positioning; motor control comprising delivering high-speed motor control signals to the arm's actuators, enabling smooth and precise movement; and sensor integration comprising integrating sensor data from various sources (e.g., optical, capacitive, pressure sensors and other sensor types as would be recognized by the person of ordinary skill), providing a comprehensive view of the robotic system's state. In illustrative examples, the robotic arm I/O interface 240 may be configured to generate motor commands to accurately position dental instruments within the patient's mouth, given a reference point of beginning or starting point and a destination. The robotic arm I/O interface 240 may be configured to execute intricate dental procedures by controlling the robotic arm's movements with high precision and accuracy.

In the depicted implementation, the robot I/O interface 230 includes the safety interlock Input/Output (I/O) interface 245. In the depicted implementation, the safety interlock I/O interface 245 includes circuitry and programming configured to govern robotic system's operation within predetermined safety boundaries, preventing accidents and damage to the patient or surrounding equipment. For example, the safety interlock I/O interface 245 may include sensors, such as for example optical, capacitive, and pressure transducers, which permit the safety interlock I/O interface 245 to continuously monitor the robot's movement and interaction with the environment. The safety interlock I/O interface 245 may interface with the end effector I/O interface 235 and/or the robotic arm I/O interface 240 to prevent unintended motions or collisions by generating warning signals or halting the robot when safety thresholds are breached. For instance, the safety interlock I/O interface 245 may be configured such that if capacitive sensor information indicates a patient's head approaches the operating zone within a predetermined distance, the safety interlock I/O interface 245 may trigger an alarm. In such a scenario, the safety interlock I/O interface 245 may be configured to initiate an emergency shutdown protocol for portions of the dental robot 110. In another example, during a procedure involving a high-speed drill, the safety interlock I/O interface 245 verifies that the drill bit is securely seated before allowing the robot to initiate rotation, thus preventing loose debris from being ejected into the patient's mouth or surrounding area.

In the depicted implementation, the processor 200 is operably coupled with the user interface 250. In various implementations, the user interface 250 may be adapted to receive input from a user or send output to a user. In some embodiments, the user interface 250 may be adapted to an input-only or output-only user interface mode. In various implementations, the user interface 250 may include an imaging display. In some embodiments, the user interface 250 may include an audio interface. In some designs, the audio interface may include an audio input. In various designs, the audio interface may include an audio output. In some implementations, the user interface 250 may be touch-sensitive. The user interface 250 may be configured to receive and process graphical input drawn using a stylus or a user's finger, in contact with a touch-sensitive surface. The user interface 250 may be configured in a mobile device hosting a software application. The processor 200 may be operably coupled with a mobile device implementing the user interface 250.

In some designs, the dental robot 110 may include an accelerometer operably coupled with the processor 200. In various embodiments, the dental robot 110 may include a GPS module operably coupled with the processor 200. In an illustrative example, the dental robot 110 may include a magnetometer operably coupled with the processor 200.

In the depicted implementation, the processor 200 is operably coupled with the communication interface 255. The communication interface 255 may comprise a network interface. The network interface may be a network communication interface. In various implementations, the network interface may be a wireless network interface. In some designs, the network interface may be a Wi-Fi interface. In some embodiments, the network interface may be a BLUETOOTH interface. In an illustrative example, the dental robot 110 may include more than one network interface. In some designs, the network interface may be a wireline interface. In some designs, the network interface may be omitted.

In some embodiments, the dental robot 110 may include an input sensor array. The input sensor array may be operably coupled with the processor 200. In various implementations, the input sensor array may include one or more imaging sensor. In various designs, the input sensor array may include one or more audio transducer. In some implementations, the input sensor array may include a radio-frequency detector. In an illustrative example, the input sensor array may include an ultrasonic audio transducer. In some embodiments, the input sensor array may include electrical signal sensing subsystems or modules configurable by the processor 200 to be adapted to implement operations, such as for example, providing signal input capability, signal output capability, signal sampling, spectral analysis, correlation, autocorrelation, Fourier transforms, buffering, filtering operations including adjusting frequency response and attenuation characteristics of spatial domain and frequency domain filters, signal or waveform recognition, pattern recognition, or anomaly detection.

The depicted memory 205 may comprise processor executable program instruction modules configurable by the processor 200 to be adapted to implement operations, such as for example, providing signal input capability, signal output capability, signal sampling, spectral analysis, correlation, autocorrelation, Fourier transforms, sample buffering, modulation, demodulation, error correction, encryption, decryption, encryption key generation, encryption key management, biometric template generation, biometric input authentication, signal filtering operations including adjusting frequency response and attenuation characteristics of time domain, spatial domain or frequency domain filters, signal or waveform recognition, pattern recognition, template matching or anomaly detection. In some embodiments, the dental robot 110 may comprise hardware subsystems or modules configurable by the processor 200 to be adapted to provide signal input capability, signal output capability, signal sampling, spectral analysis, correlation, autocorrelation, Fourier transforms, sample buffering, modulation, demodulation, error correction, encryption, decryption, encryption key generation, encryption key management, biometric template generation, biometric input authentication, signal filtering operations including adjusting frequency response and attenuation characteristics of spatial domain and frequency domain filters, signal or waveform recognition, pattern recognition, template matching or anomaly detection.

The dental robot 110 may be configured with a multimedia interface. The multimedia interface may be operably coupled with the processor 200. The multimedia interface may comprise an interface adapted to input and output of audio, video, and/or image data. In some embodiments, the multimedia interface may include one or more still image camera or video camera. In various designs, the multimedia interface may include one or more microphone. In some implementations, the multimedia interface may include a wireless communication means configured to operably and communicatively couple the multimedia interface with a multimedia data source or sink external to the dental robot 110. The multimedia interface may include interfaces adapted to send, receive, or process encoded audio or video. The multimedia interface may include one or more video, image, or audio encoder. The multimedia interface may include one or more video, image, or audio decoder. The multimedia interface may include interfaces adapted to send, receive, or process one or more multimedia stream. The multimedia interface may include a GPU. The multimedia interface may be omitted. The multimedia interface may be implemented in a mobile device operably coupled with the processor 200. For example, the multimedia interface may be configured in a mobile device hosting a software application.

The dental robot 110 may comprise a digital-to-analog converter configured to convert a signal or value stored in digital form into electrical output energy. The electrical output energy may be applied to one or more analog outputs. The digital-to-analog converter may be configurable by the processor 200. The digital-to-analog conversion resolution may be configurable by the processor 200. The dental robot 110 may include one or more filters configurable by the processor 200 as a reconstruction filter to remove frequencies above the Nyquist limit. The dental robot 110 may include one or more amplifiers with gain configurable by the processor 200. For example the processor 200 may configure the gain of one or more amplifiers to adjust the output amplitude of one or more output signal.

The dental robot 110 may comprise an analog-to-digital converter configured to convert electrical input energy from one or more input into digital form for use by the processor 200. The analog-to-digital converter resolution and sampling rate may be configurable by the processor 200. The dental robot 110 may include one or more filters configurable by the processor 200 to selectively remove and/or pass certain frequencies from received input energy. For example, the dental robot 110 may include a low pass filter configurable by the processor as an anti-aliasing filter. The anti-aliasing filter may have a pass band configurable by the processor 200 to reject input frequencies above half the configured sampling rate of the analog-to-digital converter. The dental robot 110 may include impedance matching circuitry. The impedance matching circuitry may be configurable by the processor 200 to match input impedance with the impedance of a signal source. Matching electrode input impedance with the impedance of the signal source may permit efficiently receiving signal energy from the signal source, achieving more accurate measurement as a result of mitigating signal loss that might result from impedance mismatch.

Useful implementation examples of one or more of the features illustrated by FIG. 2 may include, but are not limited to, personal computers, servers, tablet PCs, smartphones, or other computing devices. In some embodiments, multiple dental robot 110 devices may be operably linked to form a computer network in a manner as to distribute and share one or more resources, such as clustered computing devices and server banks/farms. In some embodiments, an exemplary dental robot 110 design may be realized in a distributed implementation. A dental robot 110 design may be partitioned between a client device, such as, for example, a phone, and, a more powerful server system with greater resources, such as for example, computation, memory or storage capacity. In various designs, a dental robot 110 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work. In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary dental robot 110 may be configured to operate on a device with less processing power, such as, for example, various gaming consoles or consumer devices such as Internet of Things (IoT) or Edge Computing (EdgCo) devices, which may not have sufficient processor power, or a suitable CPU architecture, to adequately support dental robot 110. Various embodiment designs configured to operate on a such a device with reduced processor power may work in conjunction with a more powerful server system.

Figure 3:
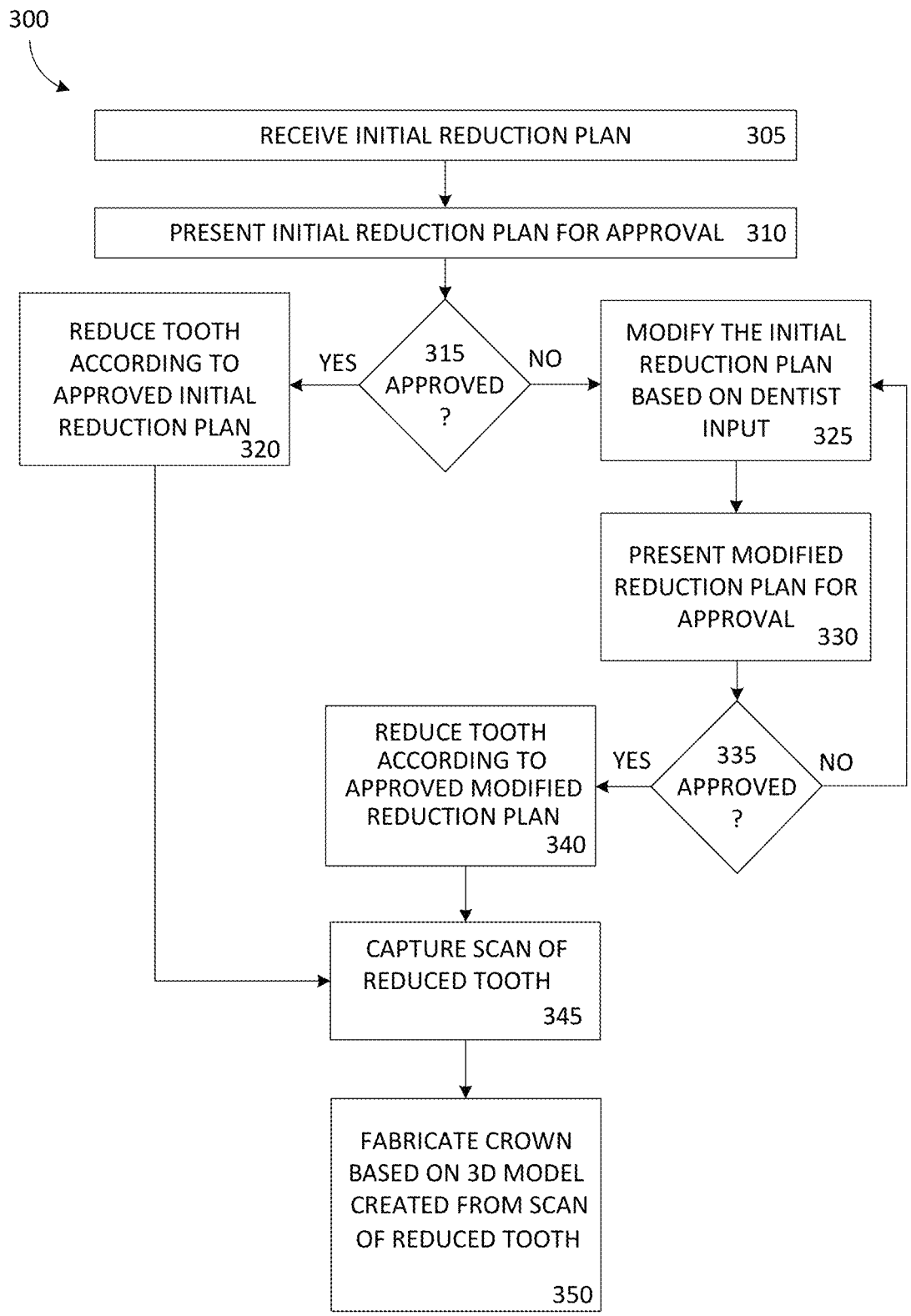
FIG. 3 depicts a process flow of an exemplary robotic dentistry engine (RDE) configured to integrate the expertise of a human dentist into confirming and adjusting reduction plans for crown preparation.

FIG. 3 depicts a process flow of an exemplary robotic dentistry engine (RDE) configured to integrate the expertise of a human dentist into confirming and adjusting reduction plans for crown preparation.

In FIG. 3, the depicted method 300 is given from the perspective of the robotic dentistry engine (RDE) 220 implemented via processor-executable program instructions executing on the dental robot 110 processor 200, depicted in FIG. 2. In some implementations, the RDE 220 may execute as a cloud service communicatively and operatively coupled with system services, hardware resources, or software elements local to and/or external to the dental robot 110. In some designs, the RDE 220 may collaboratively execute both on the processor 200 as a process local to the dental robot 110 and on another processor remote from the dental robot 110.

The depicted method 300 begins at step 305 with the processor 200 receiving an initial reduction plan.

The method continues at step 310 with the processor 200 presenting the initial reduction plan for approval. The processor 200 may present the initial reduction plan to a dentist. The processor 200 may present the initial reduction plan via a user interface.

At step 315, the processor 200 performs a test to determine if the reduction plan was approved. The processor 200 may determine if the reduction plan was approved based on evaluating input received by a user interface operably coupled with the processor 200.

Upon a determination by the processor 200 at step 315 that the reduction plan was approved, the method continues at step 320. Upon a determination by the processor 200 at step 315 that the reduction plan was not approved, the method continues at step 325. In this example, non-approval of the reduction plan is a rejection of the reduction plan.

At step 320, the processor 200 reduces the tooth according to the approved reduction plan. The processor 200 may reduce the tooth using a reducing tool configured in the dental robot 110, depicted by at least FIG. 1. Then, the method continues at step 345.

At step 325, the processor 200 modifies the rejected reduction plan based on dentist input.

At step 330, the processor 200 presents the modified reduction plan for approval. The processor 200 may present the modified reduction plan to a dentist. The processor 200 may present the modified reduction plan via a user interface.

At step 335, the processor 200 performs a test to determine if the modified reduction plan was approved. The processor 200 may determine if the modified reduction plan was approved based on evaluating input received by a user interface operably coupled with the processor 200.

Upon a determination by the processor 200 at step 335 that the modified reduction plan was approved, the method continues at step 340. Upon a determination by the processor 200 at step 335 that the modified reduction plan was not approved, the method continues at step 325. In this example, non-approval of the modified reduction plan is a rejection of the modified reduction plan.

At step 340, the processor 200 reduces the tooth according to the approved modified reduction plan. The processor 200 may reduce the tooth using a reducing tool operably coupled with the dental robot 110, depicted by at least FIG. 1. The dental robot may be configured to anesthetize tissue in the area surrounding the tooth before reducing the tooth for crown preparation. For example, the dental robot may be configured to inject an anesthetic into an area surrounding the tooth to be reduced.

At step 345, the processor 200 captures a three-dimensional (3D) scan of the reduced tooth. The 3D scan may be an optical scan. The processor 200 may capture the 3D scan of the tooth using a scanning device operably coupled with the dental robot 110, depicted by at least FIG. 1.

At step 350, the processor 200 fabricates a crown based on a digital 3D model created from the 3D scan of the reduced tooth. The processor 200 may fabricate the crown using a dental mill operably coupled with the dental robot 110, depicted by at least FIG. 1.

In some implementations, the method may repeat. In various implementations, the method may end.

Figure 4:
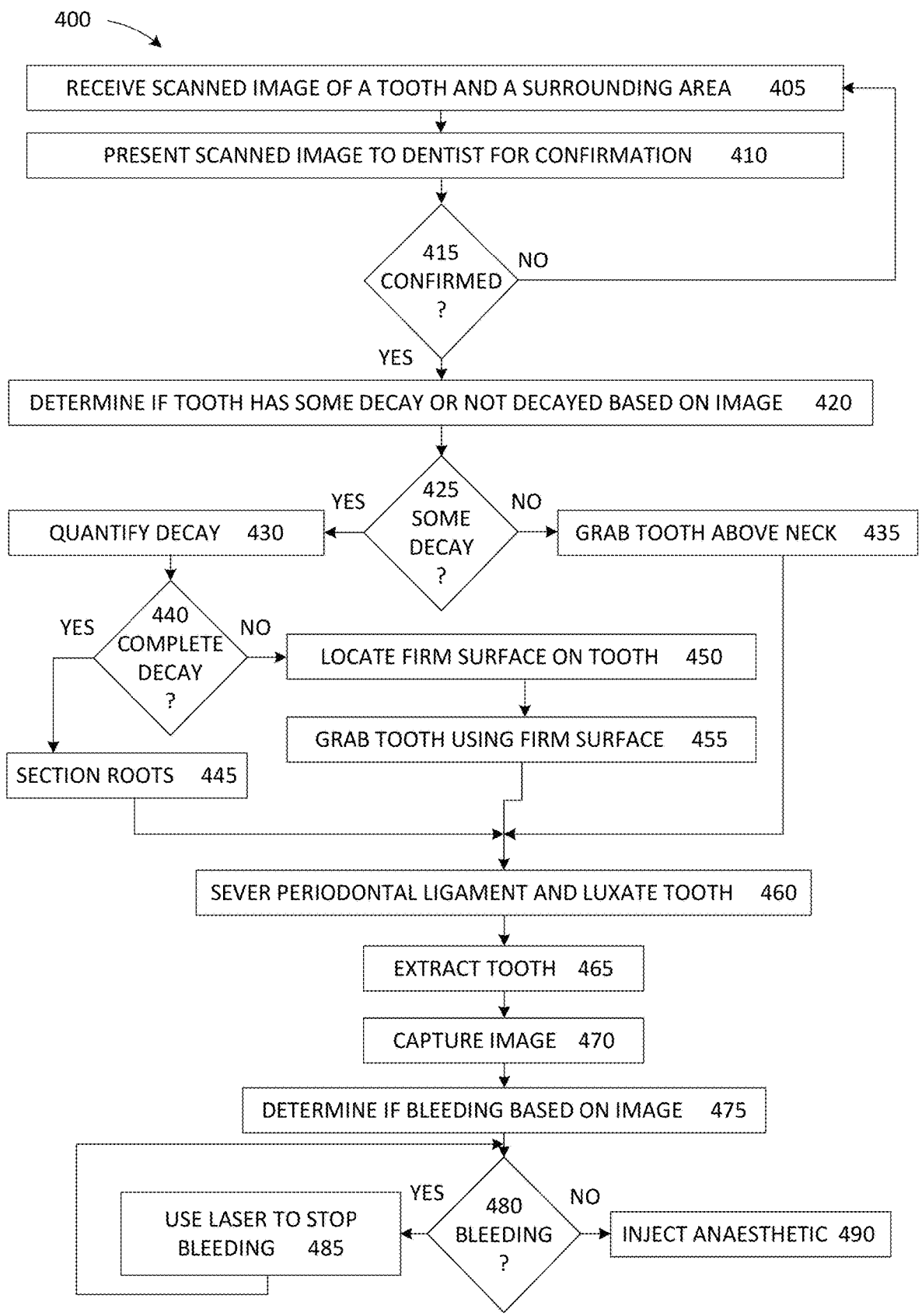
FIG. 4 depicts a process flow of an exemplary robotic dentistry engine (RDE) configured to integrate the expertise of a human dentist into confirming and adjusting extraction plans for tooth extraction.

FIG. 4 depicts a process flow of an exemplary robotic dentistry engine (RDE) configured to integrate the expertise of a human dentist into confirming and adjusting extraction plans for tooth extraction.

In FIG. 4, the depicted method 400 is given from the perspective of the robotic dentistry engine (RDE) 220 implemented via processor-executable program instructions executing on the dental robot 110 processor 200, depicted in FIG. 2. In some implementations, the RDE 220 may execute as a cloud service communicatively and operatively coupled with system services, hardware resources, or software elements local to and/or external to the dental robot 110. In some designs, the RDE 220 may collaboratively execute both on the processor 200 as a process local to the dental robot 110 and on another processor remote from the dental robot 110.

The depicted method 400 begins at step 405 with the processor 200 receiving a scanned image of a tooth. The scanned image of the tooth may be an image resulting from an optical scan, an X-ray or a CT scan. The scanned image of the tooth may further comprise an image of an area surrounding the tooth. The image of the area surrounding the tooth may comprise an image of a patient's mouth. The image of the patient's mouth may depict more than one tooth.

The method continues at step 410 with the processor 200 presenting the scanned image for confirmation that the tooth depicted by the scanned image is a tooth targeted for extraction. The processor 200 may present the scanned image to a dentist for confirmation. The processor 200 may present the scanned image via a user interface. The processor 200 may request the dentist to provide confirmation that the tooth depicted by the scanned image is the tooth targeted for extraction.

At step 415, the processor 200 performs a test to determine if the tooth depicted by the scanned image is confirmed to be the tooth targeted for extraction. The processor 200 may determine if the tooth depicted by the scanned image is confirmed by the dentist as the tooth targeted for extraction. The processor 200 may evaluate input received by a user interface operably coupled with the processor 200, to determine if the tooth depicted by the scanned image is confirmed. The processor 200 may determine if the tooth depicted by the scanned image is the tooth targeted for extraction based on object detection techniques such as would be known to one of ordinary skill. For example, the processor 200 may use an image-based object detection algorithm trained to identify one or more individual teeth depicted in an image. The processor 200 may execute a segmentation image processing algorithm to segment the scan of the patient's mouth into multiple images. Each image of the segmented multiple images may comprise an image of at least one tooth. The processor 200 may execute an identification image processing algorithm to locate and identify individual teeth. The identification image processing algorithm may locate and identify individual teeth by numbers determined as a function of the position of individual teeth in the scan of the patient's mouth. The identification image processing algorithm may locate and identify individual teeth in accordance with a numbering system. For example, in the Upper Jaw (Maxillary Arch) Teeth may be numbered from 1 to 16, starting from the upper right third molar (wisdom tooth) and moving clockwise to the upper left third molar. In the Lower Jaw (Mandibular Arch) Teeth may be numbered from 17 to 32, starting from the lower left third molar and moving clockwise to the lower right third molar. The object detection algorithm may be trained to identify one or more individual teeth using ground truth images each depicting an individual tooth labeled with a true identification of the depicted individual tooth.

The processor 200 may compare a tooth number determined by the object detection algorithm with a tooth number from an extraction plan. Upon a determination the tooth number determined by the object detection algorithm matches the tooth number provided by the extraction plan, the processor 200 may determine the depicted tooth is the tooth targeted for extraction. Upon a determination the depicted tooth is the tooth targeted for extraction using the image-based object detection algorithm, the processor 200 may present an image of the tooth to the dentist for confirmation. The image of the tooth may be presented for confirmation by the processor 200 with an indication of the tooth number determined by the image-based object detection algorithm. The image of the tooth may be presented by the processor 200 for confirmation with an indication the image-based object detection algorithm has determined the depicted tooth is the tooth targeted for extraction. The image-based object detection algorithm may be configured with a tooth identification neural network. The tooth identification neural network may be, for example, an implementation of an open source object detection framework. An image processing pipeline may feed the tooth identification neural network with processed images. The image processing pipeline may perform one or more of scaling, normalization, greyscale conversion, histogram equalization, edge detection or other image processing operations as would be known by one of ordinary skill. Processed images output from the image processing pipeline may feed feature detectors at inputs to the tooth identification neural network. Feature detectors may be configured at the inputs to the model from the image processing pipeline to detect any useful features as would be recognized by one of ordinary skill.

In the depicted implementation, upon a determination by the processor 200 at step 415 that the tooth depicted by the scanned image was not confirmed as the tooth targeted for extraction, the method continues at step 405. In case the tooth depicted by the scanned image was not confirmed as targeted for extraction, another scanned image depicting another tooth may be provided to the dental robot at step 405.

The dental robot may be configured to anesthetize tissue in the area surrounding a tooth before extracting the tooth. For example, the dental robot may be configured to inject an anesthetic into an area surrounding the tooth targeted for extraction.

Upon a determination by the processor 200 at step 415 that the tooth depicted by the scanned image was confirmed as the tooth targeted for extraction, the method continues at step 420.

At step 420, the processor 200 determines if the tooth targeted for extraction has some decay or no decay based on analysis of a scanned image of the tooth by the processor 200. The determination by the processor 200 at step 420 of whether the tooth has some decay or has no decay may be implemented as a classification problem solved by a trained decay classification machine learning model. The decay classification machine learning model may be trained to classify an image of the tooth as depicting at least some decay or no decay determined as a function of the image. An example of the decay classification neural network may comprise at least one Convolutional Neural Network (CNN). The at least one CNN comprising the decay classification neural network may be configured with supervised training on labeled ground truth images. The labeled ground truth images used to train the decay classification neural network may comprise labeled images depicting decayed or healthy teeth. Each labeled ground truth image may be labeled with the correct classification of decayed or healthy tooth. The decay classification neural network may be trained to classify a tooth image as showing a decayed or healthy tooth, using the training data. Other machine learning models, neural network architectures, training data, training algorithms and inference techniques may be employed to implement the decay classification machine learning model, as would be known by one of ordinary skill. An image processing pipeline may feed the decay classification machine learning model with processed images. The image processing pipeline may perform one or more of scaling, normalization, greyscale conversion, histogram equalization, edge detection or other image processing operations as would be known by one of ordinary skill. Processed images output from the image processing pipeline may feed feature detectors at inputs to the decay classification machine learning model. Feature detectors may be configured at the inputs to the model from the image processing pipeline to detect any useful features as would be recognized by one of ordinary skill. Alternatively, the dentist may classify the tooth as having some decay or not decayed, via a user interface.

At step 425, the processor 200 performs a test to determine if the tooth can be extracted using a non-surgical extraction technique in the case of no decay, or if further analysis of the decay state of the tooth may permit selection of a more advantageous extraction technique for a tooth classified as having at least some decay. Upon a determination by the processor 200 at step 425 that the tooth targeted for extraction has no decay, the method continues at step 435. Upon a determination by the processor 200 at step 425 that the tooth targeted for extraction has some decay, the method continues at step 430.

At step 430 the processor 200 quantifies the extent of decay in the tooth targeted for extraction. In the depicted implementation, at step 430 the processor 200 may determine the decay state of the tooth as one of: completely decayed; or decayed, but not completely decayed. The processor 200 may determine the decay state of the tooth targeted for extraction based on quantifying the decay. The processor 200 may quantify the decay of the tooth targeted for extraction based on analysis of a scanned image.

The scanned image used by the processor 200 to quantify the decay at step 430 may be a different scanned image than the scanned image received by the processor 200 at step 405. For example, at step 430, the processor 200 may capture another scanned image of the tooth. The scanned image captured at step 430 may be captured using a different imaging device or from a different perspective than the scanned image of the tooth received by the processor 200 at step 405. The scanned image of the tooth captured at step 430 used to determine extent of decay in the tooth may be higher resolution than the scanned image of the tooth received by the processor 200 at step 405. The scanned image of the tooth captured at step 430 may be a result of an optical scan, an X-ray or a CT scan. Using an X-ray or a CT scan may improve decay extent localization and/or quantification relative to using an optical scan, by exposing internal tooth structures and/or material to decay detection algorithms. Such decay detection algorithms may use this enhanced data showing internal structure to indicate decay that is not visible on exterior tooth surfaces. The scanned image of the tooth captured at step 430 may be multiple scanned images captured from different perspectives. For example, at step 430 scanned images of the tooth may be captured from above the tooth to show the tooth's upper biting surface, from a point facing outward from the mouth (for example from a point inside the mouth) or from a point facing inward to the mouth (for example from a point outside the mouth). Capturing multiple scanned images of the tooth and using the multiple scanned images to quantify an extent of decay in the tooth may improve decay extent quantification and localization, by exposing a comprehensive view of tooth surfaces to decay extent detection algorithms. Such decay extent detection algorithms may use this enhanced data to determine the extent of decay in a tooth, increasing the accuracy of extraction technique selection based on the extent or degree of decay.

The quantification of decay by the processor 200 at step 430 may be implemented as an identification problem solved by a trained decay extent determination machine learning model. The decay extent determination machine learning model may comprise a decay extent determination neural network. An example of the decay extent determination neural network may be a Convolutional Neural Network (CNN) configured by supervised training on labeled ground truth images. The labeled ground truth images may be subdivided into a mesh or grid of virtual digital cells covering the surface of decayed and healthy teeth. Each cell in the grid of virtual digital cells in the ground truth images may be labeled as decayed or healthy. The labeling for each image may include the percentage of grid cells for that tooth which show decayed tooth material. The decay extent determination neural network may be trained using the labeled ground truth images, to determine the percentage of grid cells showing decayed tooth material. The decay extent determination neural network may be trained using the labeled ground truth images, to determine the individual decay state of each cell in the grid. In this example, the determination of "completely decayed" may be made by the processor 200 based on comparing the percentage of grid cells showing decay in an individual tooth to a predetermined threshold percentage representing complete decay. The predetermined threshold percentage may be adjustable by the dentist in real time while viewing images of the patient's teeth, permitting the dentist to adapt a visualization of decayed teeth presented in the user interface to the general condition of a patient's teeth. For example, by adjusting the predetermined threshold percentage up or down, more or less decayed teeth may be highlighted in a visual display presented to the dentist. This facilitation may permit the dentist to isolate teeth with the greatest decay extent for earliest treatment or extraction. Other machine learning models, neural network architectures, training data, training algorithms and inference techniques may be employed to implement the decay extent determination machine learning model, as would be known by one of ordinary skill. An image processing pipeline may feed the decay extent determination machine learning model with processed images. The image processing pipeline may perform one or more of scaling, normalization, greyscale conversion, histogram equalization, edge detection or other image processing operations as would be known by one of ordinary skill. Processed images output from the image processing pipeline may feed feature detectors at inputs to the decay extent determination machine learning model. Feature detectors may be configured at the inputs to the model from the image processing pipeline to detect any useful features as would be recognized by one of ordinary skill. Alternatively, the dentist may indicate the extent of decay in the tooth targeted for extraction, via a user interface.

At step 435, the processor 200 grabs the tooth targeted for extraction above the neck of the tooth. The processor 200 may grab the tooth using an end effector operably coupled with the dental robot 110, depicted at least by FIG. 1. The end effector used to grab the tooth may be forceps.

In the depicted implementation, after the processor 200 at step 430 quantifies the extent of decay in the tooth targeted for extraction, the method continues at step 440.

At step 440, the processor 200 performs a test to determine if the tooth targeted for extraction is completely decayed or decayed, but not completely decayed, based on the quantification of the extent of decay in the tooth at step 430. The processor 200 may determine if the tooth is completely decayed based on comparing a percentage of grid cells showing decay in an individual tooth to a predetermined threshold percentage representing complete decay. Determining whether the tooth is completely decayed or decayed, but not completely decayed may permit selection of a more advantageous extraction technique for a tooth classified as having at least some decay. For example, the processor 200 may use an extraction technique selected as a function of the extent of decay determined at step 430 for the tooth targeted for extraction. The selected extraction technique may be a nonsurgical technique. The selected extraction technique may be a surgical technique. Upon a determination by the processor 200 at step 440 the tooth targeted for extraction is completely decayed, the method continues at step 445. Upon a determination by the processor 200 at step 440 the tooth targeted for extraction is decayed, but not completely decayed, the method continues at step 450.

At step 445, the processor 200 sections the roots of the tooth targeted for extraction. The processor 200 may section the roots of the tooth targeted for extraction using an end effector operably coupled with the dental robot 110, depicted at least by FIG. 1.

At step 450, the processor 200 locates a firm surface on the tooth targeted for extraction. In the depicted implementation, a firm surface on the tooth may be a surface that is not decayed. A surface that is not decayed may be identified by the processor 200 using image processing techniques disclosed herein. The processor 200 may select surface locations that are not decayed on opposing sides of the tooth, using geometric analysis of the tooth and the locations of grid cells identified as not decayed, in line with what has been disclosed herein. For example, the firm surface located by the processor 200 may be characterized by two groups of multiple adjoining grid cells. Each group of multiple adjoining grid cells may form a contiguous area on the tooth surface, providing strong and stable gripping areas on opposing sides of the tooth as a result of the non-decayed grid cell groups. Two groups of grid cells may be located on opposing sides of the tooth such that a gripper could securely grab the tooth near a centroid of a group of grid cells on each side of the tooth, applying gripping force to non-decayed areas on the opposing sides of the tooth. In an illustrative example, the number of grid cells forming a contiguous firm location for gripping may be adjustable as a predetermined threshold. Given a minimum number of grid cells and the grid cell size configuration for the decay extent determination algorithm, the processor 200 may determine the surface area of each firm location for gripping. The processor 200 may be configured to approve or not approve extraction of a tooth that is decayed, but not completely decayed, based on the availability of a predetermined minimum surface area of the firm locations for gripping that can be identified on the tooth. Alternatively, the dentist may indicate a location on the tooth of one or more firm surface for gripping, via a user interface.

At step 455, the processor 200 uses an end effector operably coupled with the dental robot 110 to grab the tooth targeted for extraction using the firm surfaces identified at step 450. The processor 200 may use forceps to grab the tooth.

At step 460, the processor 200 severs a periodontal ligament associated with the tooth and luxates the tooth. The processor 200 may sever the periodontal ligament and luxate the tooth using one or more end effectors operably coupled with the dental robot 110, depicted by at least FIG. 1.

At step 465, the processor 200 extracts the tooth. The processor 200 may extract the tooth using one or more end effectors operably coupled with the dental robot 110, depicted by at least FIG. 1. The one or more end effectors used to extract the tooth may comprise forceps.

At step 470, the processor 200 captures an image depicting the location in the patient's mouth where the tooth targeted for extraction was extracted.

At step 475, the processor 200 determines if the patient is bleeding from the site where the tooth was extracted. The processor 200 may use image processing algorithms known to those of ordinary skill to determine bleeding identified as a function of the image. For example, color histograms of images of the extraction site before extraction and after extraction may be compared to identify the presence of increased Red color in the image after extraction. The histograms may be compared by the processor 200 using correlation-based techniques as would be known by one of ordinary skill. In this example, a correlation coefficient below a predetermined threshold may indicate bleeding for color histograms of the extraction site before and after extraction. The correlation may be computed by the processor 200 in the frequency domain, reducing computational load. In an illustrative example, increased Red color may indicate bleeding. In another example, a video of the extraction site captured after extraction may be processed using optical flow algorithms known by one of ordinary skill in the art of video coding, to identify fluid flowing from the extraction site. Fluid flowing from the extraction site may indicate bleeding. In an illustrative example, the processor 200 may determine the severity of bleeding measured as a function of the number of pixels changing between video frames. The severity of bleeding may be compared by the processor 200 with a predetermined threshold severity and bleeding severity exceeding the threshold may trigger a notification to the dentist. Other techniques useful to determine bleeding based on an image of the extraction site may be employed as would be recognized by one of ordinary skill. The dentist may determine if there is bleeding from the area surrounding the extracted tooth. In a case wherein the dentist determines there is bleeding, the dentist may indicate the location or site of the bleeding using the user interface to the dental robot. For example, the dentist may indicate bleeding from the socket where the tooth was extracted. The dental robot may be programmed and configured to implement one or more actions to stop the bleeding.

At step 480, the processor 200 performs a test to determine if the patient is bleeding from the extraction site, based on analysis of the image captured at step 470. The determination of whether the patient is bleeding may be based on a threshold in line with what has been discussed above. Upon a determination the patient is bleeding, the method continues at step 485. Upon a determination the patient is not bleeding, the method continues at step 490.

At step 485, the processor 200 uses a laser to stop the bleeding. The laser may be an end effector operably coupled with the dental robot, depicted at least by FIG. 1.

At step 490, the processor 200 injects an anesthetic at or near the extraction site. The processor 200 may inject the anesthetic using an end effector operably coupled with the dental robot, depicted at least by FIG. 1. The anesthetic may be Novocaine®.

In some implementations, the method may repeat. In various implementations, the method may end.

With reference to FIGS. 5-9, the exemplary dental robot 110 comprises electronic and mechanical hardware, a computer implemented control system and interfaces permitting a human dentist to collaborate with the dental robot 110.

In the depicted implementation, the dental robot 110 may comprise a plurality of functional units, such as for example a robotic arm, articulators, end effectors, sensors, and a haptic device for remote operation. The dental robot 110 may be configured as a 6-Degree-Of-Freedom (DOF) robotic manipulator with six motors to actuate the manipulator. The haptic device may be programmed to obtain the dentist's hand motion and architecture and map the motion into the manipulator's workspace. In an illustrative example, because of the tendon-sheath design, the 6-DOF robotic manipulator positions motor transmission component outside the patient's mouth, reducing the space required within the patient's mouth. The 6-DOF robotic manipulator is configured to position and use end effectors for access to all teeth without requiring additional space in the patient's mouth for the dentist's hands. Performing procedures within the patient's mouth without requiring space in the mouth for the dentist's hands may enable some procedures for patients with smaller mouths, such as smaller children for example. Joint movement parameters may be calculated by the control system using inverse kinematics analytically to determine actuation commands. The actuation commands determined by the control system may be sent by the control system to the motors, to drive the manipulator and perform crown preparation and extraction operations. In the mechanical design, a tendon-sheath mechanism design and asymmetric configuration reduce the form factor and physical footprint of the manipulator and maximize the designed workspace to cover a real human oral cavity.

The 6-DOF manipulator robotic arms permit precise movement in various directions to position the end effectors such as luxators, elevators and forceps for tooth extraction and to position an ablation tool to reduce a tooth for crown preparation. The 6-DOF manipulator may comprise two cylindrical joints, two revolute joints, a wrist joint with 2 orthogonal DOF, and a dental handpiece configured as an end effector. For miniaturization, a tendon-sheath mechanism may be used. Each joint may be actuated by a pair of steel threads, also known as the tendons. The sheaths are auxiliary structures for enveloping the tendons to reduce the friction between tendons and the outer shells. The tendon actuation mechanism permits the motors to be located outside the manipulator. Thus, powerful motors can be utilized without affecting the size of the manipulator.

The control system may be configured to receive a digital reduction plan or digital tooth extraction plan. The digital reduction plan or digital tooth extraction plan may be an approved or modified digital reduction plan. The digital reduction plan or digital tooth extraction may be converted as a system input signal by the control system. The digital reduction plan or digital tooth extraction system input may be transferred into manipulator motions in a 6-Degree of Freedom (DOF) spatial data space and mapped from the dentist's reduction plan or tooth extraction plan workspace into the manipulator's workspace. The spatial data may be processed by the manipulator control system. The manipulator control system may be a commercially available embedded control system configured and programmed to determine and generate corresponding motor commands as a function of operator input, reduction plans, three-dimensional digital maps of the tooth being treated and input from sensors such as accelerometers and ultrasonic or infrared proximity sensors. The generated motor commands may be sent by the manipulator control system to the digital servo motors to drive the manipulator and to perform crown preparation and tooth extraction operation motions. During an inverse kinematics procedure, the manipulator control system may be guided by software considering characteristics of the manipulator, to connect the hardware and software in the system.

The control system may also be configured to permit a dentist to serve as the robot operator and their hand motion inputs to a haptic device may be digitized by the haptic device and converted as a system input signal. The digitized dentist hand motions may then be transferred into the 6-Degree of Freedom (DOF) spatial data space and mapped from the dentist's workspace into the manipulator's workspace. The spatial data may be processed by the manipulator control system, in line with what has been discussed hereinabove.

In an exemplary crown preparation mode the dental robot may be configured to prepare a tooth to receive a crown by reducing the tooth according to a reduction plan, using a reducing tool such as an ablation tool guided by a control system governing motors configured to move manipulator arms to position the ablation tool according to an approved reduction plan.

In an exemplary crown preparation mode the dental robot may be configured to position an optical scanner or camera proximal to the prepared tooth in the patient's mouth, using a control system governing motors configured to move manipulator arms to position the optical scanner or camera to capture the optical scan of the tooth prepared to receive the formed crown. The milling machine then uses a digital milling plan created from the prepared tooth, increasing accuracy and quality of the milled crown.

In an exemplary tooth extraction mode the dental robot may be configured to extract a tooth by severing a periodontal ligament and luxating the tooth, using an elevator/luxator, forceps and/or surgical handpiece guided by a control system governing motors configured to move manipulator arms to position the elevator/luxator, forceps and/or surgical handpiece proximal to the tooth targeted for extraction.

To control the robot manipulator arms with motors, the depicted dental robot 110 is configured with software-implemented control algorithms that utilize sensor input to move end effectors as needed to perform crown preparation operations. These algorithms are based on feedback control principles and can be implemented using programming languages such as C++, Java, Rust or Python. Various operating systems, such as Windows, Linux, and macOS, provide a platform for running dental robot software applications. The control algorithms use data from sensors, such as cameras and proximity sensors, to track the position of the reducing tool relative to the tooth and other surrounding structures. A dental robot implementation may be configured with various position sensors, such as encoders and potentiometers, to provide precise feedback control. Force/torque sensors may be integrated with the dental robot control system to ensure accurate force control and prevent excessive stress on instruments or tissues. This data is then used to adjust the movement of the end effectors to ensure accurate and precise placement of an end effector. A dental robot implementation may be configured to use various control algorithms that would be known to one of ordinary skill. For example, Proportional-Integral-Derivative (PID) and Model Predictive Control (MPC) algorithms are well known in industrial control systems. PID and MPC algorithms and controllers may be adapted to robotic dentistry for real-time optimization and precise control of manipulator arms and end effectors.

The control system is responsible for coordinating the movements of the robot's motors based on the control algorithms. This coordination may involve a feedback loop where the robot's actual position is compared with the desired position, and adjustments are made as necessary.

In an illustrative example, a dental robot control algorithm may generate commands to servo motors for moving robotic arms connected to the dental robot. The control algorithm may receive input comprising a destination point in three-dimensional space. The dental robot is configured with sensors and a memory configured to store the starting point in three-dimensional space. The starting point is the current location of an end effector in three-dimensional space. The algorithm should determine commands to the servo motors to move the end effector from the current point to the destination point. An exemplary control algorithm is provided below in the form of python pseudocode.

Example Servo Motor Command Generation Algorithm for One Dental Robot Arm

Input Parameters

Destination Point ('destination_x', 'destination_y', 'destination_z'): The 3D coordinates of the target location.

Starting Point ('current_x', 'current_y', 'current_z'): The current 3D position of the end effector, stored in memory and provided by sensors. The 3D position of the end effector may include output from shaft encoders operably coupled with one or more servo motors.

Algorithm Steps

1. Calculate Displacement Vectors
   Compute the displacement vector from the current point to the destination point: 'displacement_vector=(destination_x-current_x, destination_y-current_y, destination_z-current_z)'.
2. Normalize Displacement Vector
   Normalize the displacement vector to a unit vector: 'normalized_displacement_vector=displace_men_vector/magnitude(displacement_vector)'.
   This step ensures that the movement direction is consistent with the arm's kinematics.
3. Determine Servo Motor Movements
   Calculate the desired angles for each servo motor based on the normalized displacement vector and the robot arm's geometric configuration (e.g., length of segments, joint axes).
4. Generate Commands for Servo Motors
   Based on the calculated angles, generate commands to move each servo motor towards its target angle. The commands can be in the form of Pulse-width modulation (PWM) values or other suitable control signals.
5. Store Intermediate Positions
   If desired, store intermediate positions of the end effector during movement in memory for later reference or as a safety feature.

Example Implementation (Pseudocode)

```python
def generate_servo_commands(destination_x, destination_y, destination_z, current_x, current_y, current_z):
    #1. Calculate Displacement Vector
    displacement_vector=(destination_x-current_x,
        destination_y-current_y,
        destination_z-current_z)
    #2. Normalize Displacement Vector
    magnitude_displacement_vector=sqrt (sum ([x**2 for x in displacement_vector]))
    normalized_displacement_vector=tuple (x/magnitude_displacement_vector for x in displacement_vector)
    #3. Determine Servo Motor Movements
    #Assuming a basic geometric configuration with equal segment lengths and orthogonal joint axes, adjust configuration and use depending on implementation constraints
    desired_angles_servos=[ ]
    for i, _in enumerate(displacement_vector):
        desired_angle_servo=a tan 2(normalized_displacement_vector [i], normalized_displacement_vector [(i-1) % 3])
        desired_angles_servos.append (desired_angle_servo)
    #4. Generate Commands for Servo Motors
    servo_commands=[ ]
    for angle_servo in desired_angles_servos:
        command_servo=int(angle_servo*10) # Assuming PWM control with a range of 0-100
        servo_commands.append (command_servo)
    return servo_commands
#Example Usage
destination_point=(1.2, 3.5, 4.8)
current_point=(0.0, 0.0, 0.0)
```

```
servo_commands=generate_servo_commands(destina-
    tion_point[0],
    destination_point[1],
    destination_point[2],
    current_point[0],
    current_point[1],
    current_point[2])
print ("Servo Commands:", servo_commands)
'''
```

Figure 5:
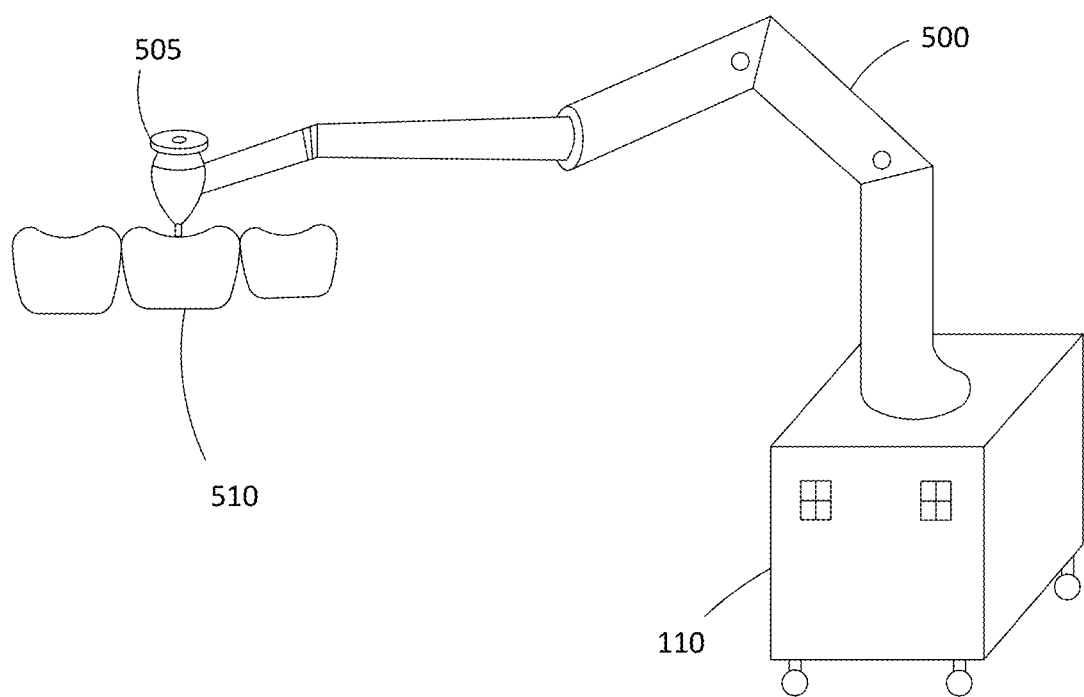
FIG. 5 depicts an exemplary dental robot performing tooth reduction using a dental handpiece in an exemplary crown preparation mode.

FIG. 5 depicts the exemplary dental robot 110 performing tooth reduction using a dental handpiece in an exemplary crown preparation mode. In FIG. 5, the dental robot 110 is configured to manipulate the robotic arm 500 to position the dental handpiece 505 proximal to the tooth 510 being reduced.

Figure 6:
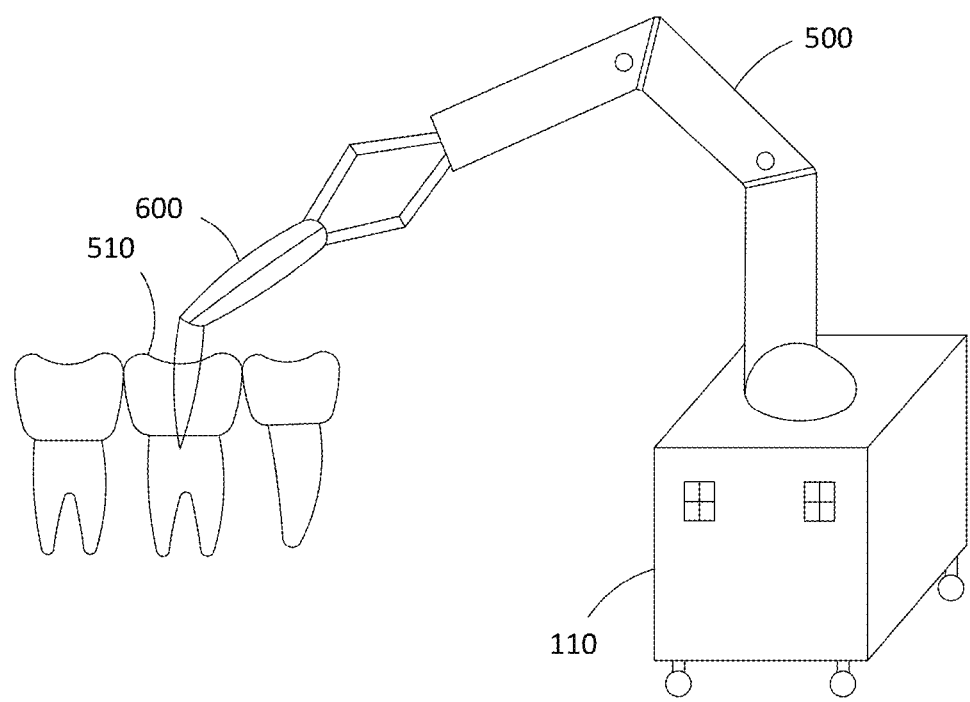
FIG. 6 depicts an exemplary dental robot severing a periodontal ligament using a luxator/elevator in an exemplary tooth extraction mode.

FIG. 6 depicts the exemplary dental robot 110 severing a periodontal ligament using a luxator/elevator in an exemplary tooth extraction mode. In FIG. 6, the dental robot 110 is configured to manipulate the robotic arm 500 to position the luxator/elevator 600 proximal to the tooth 510 targeted for extraction.

Figure 7:
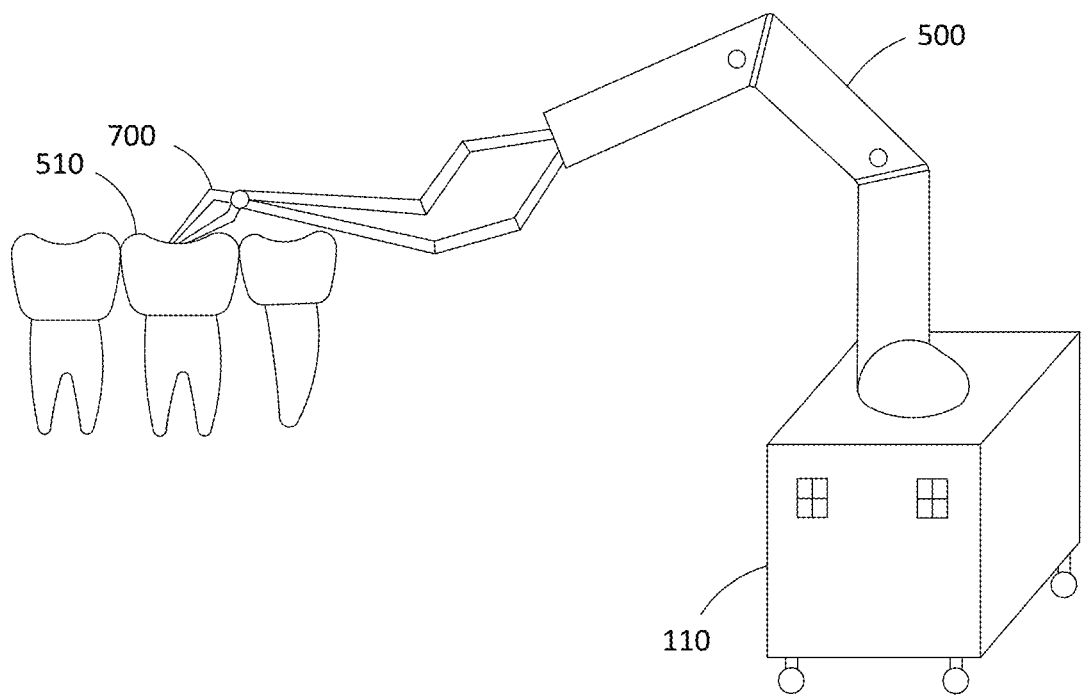
FIG. 7 depicts an exemplary dental robot extracting a tooth using dental extraction forceps in an exemplary tooth extraction mode.

FIG. 7 depicts the exemplary dental robot 110 extracting a tooth using dental extraction forceps in an exemplary tooth extraction mode. In FIG. 7, the dental robot 110 is configured to manipulate the robotic arm 500 to position the dental extraction forceps 700 proximal to the tooth 510 being extracted.

Figure 8:
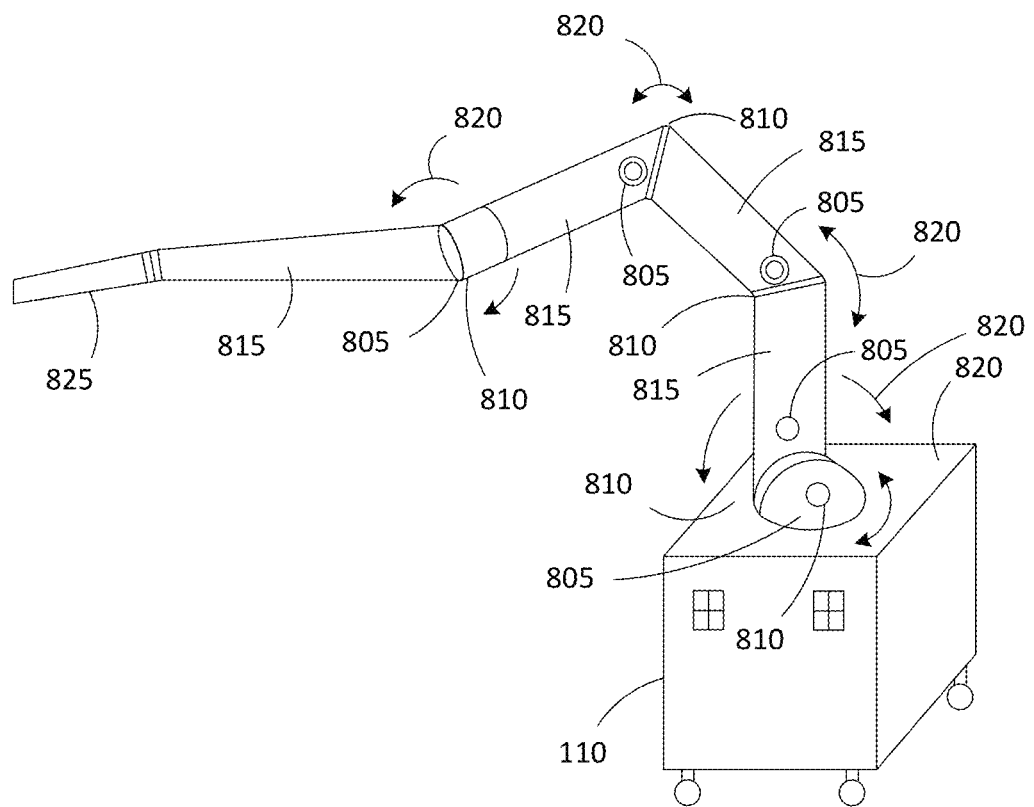
FIG. 8 depicts a detail view of an exemplary dental robot.

FIG. 8 depicts a detail view of an exemplary dental robot. In FIG. 8, the dental robot 110 includes motors 805 configured to move the manipulator arm segments 815 about the axes 820 through the manipulator joints 810. In the depicted implementation, the manipulator arm segment 825 terminates in an end effector adaptor. The manipulator arm may employ a tendon-sheath transmission system depicted by at least FIG. 9. Each of the motors 805 may be any type of motor, for example servo motors or stepper motors may be employed as would be recognized by one of ordinary skill.

In illustrative examples, the end effector adaptor may be configured to releasably engage various types of end effectors, such as for example, a reducing tool, drill, luxator/elevator, forceps or a camera.

Forceps and Elevators

An implementation may be configured with a cam mechanism adapted to engage forceps and elevators. Such a cam-based end effector adaptor design may comprise a rotating or translating component that interacts with the instrument's handle or shaft. A ball-and-socket joint may be configured to connect forceps and elevators to robotic arms, allowing for multi-axis movement and precise control. A ratchet-and-pinion mechanism may be configured to incrementally move the instrument's shaft or handle, enabling precise positioning and manipulation.

Luxators

An implementation may be configured with pneumatic or hydraulic actuation to deliver controlled forces and motions to a Luxator. Such a pneumatic or hydraulic actuation design may be achieved through mechanical linkages or fluid-powered systems.

Drills

An implementation may be configured with collet chucks adapted to releasably engage drills with robotic arms, providing a secure and precise connection between the drill shaft and the robot arm. Some examples may be designed with keyway-and-slot engagement connecting drills to robotic arms, improving alignment and positioning accuracy.

Ablation Tools

An implementation may be configured with electromagnetic or ultrasonic actuation for ablation tools, to deliver precise energy and motion control. Some examples may use magnetic or inductive coupling to connect ablation tools to robotic arms, enabling precise control over the instrument's movement.

Mechanical Techniques for Connection and Disconnection

Snap-fit mechanisms may be employed to quickly and easily connect and disconnect end effectors from robotic arms. Quick-release couplers may be used to rapidly connect and disconnect instruments, minimizing downtime and increasing efficiency. Locking mechanisms may be used to securely engage end effectors with robotic arms, preventing accidental disconnection or loss of control.

The choice of end effector for a particular robotic application may depend on factors such as the size and shape of the objects being handled, the weight of the objects, and the required precision and speed of the operation. The design of the end effector may take into account the robot's workspace, as well as any safety considerations. Controlling the end effector to perform precise and delicate operations, such as those required in dentistry, can be challenging. This often involves complex control algorithms and may require real-time feedback from sensors.

Figure 9:
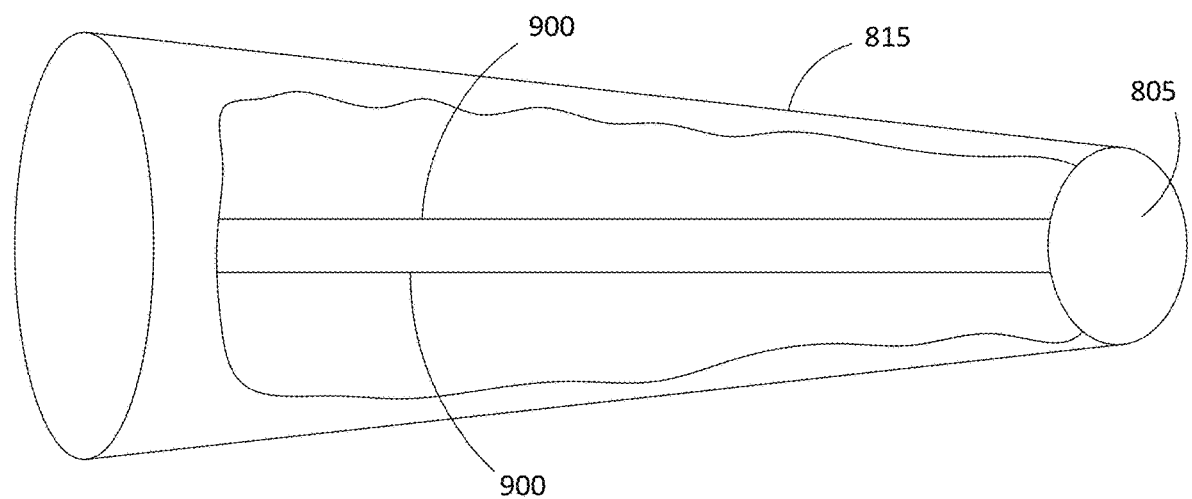
FIG. 9 depicts a detail view of an exemplary dental robot arm.

FIG. 9 depicts a detail view of an exemplary dental robot arm. In FIG. 9, the manipulator arm segment 815 includes the servo motor 805 and the tendons 900. The servo motor 805 controls the robot's movements through the tendons 900 that are actuated by the servo motors 805. This design allows for a compact and flexible robotic system, which is particularly useful in dental applications where space is limited and in six degrees of freedom configurations.

Figure 10:
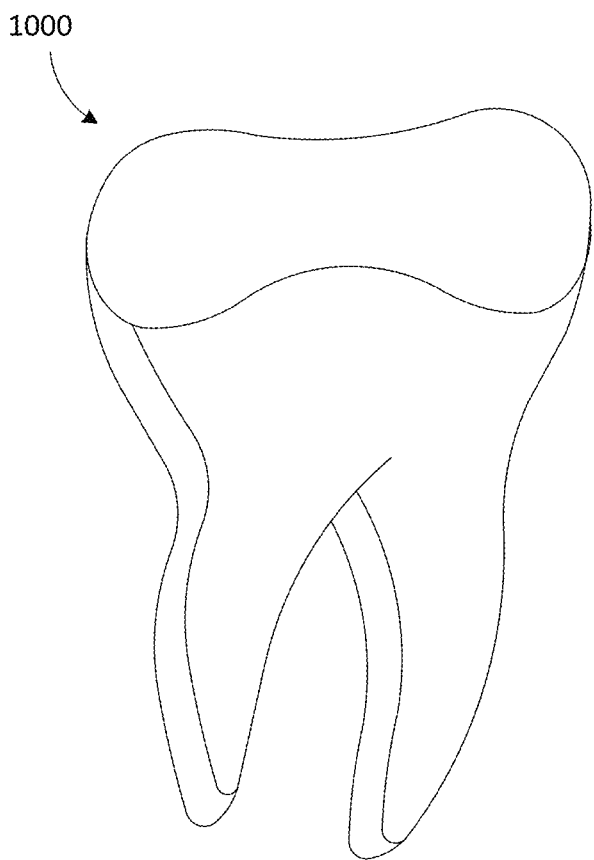
FIG. 10 depicts an exemplary tooth.

FIG. 10 depicts an exemplary tooth. In FIG. 10, the tooth 1000 is an unprepared tooth.

Figure 11:
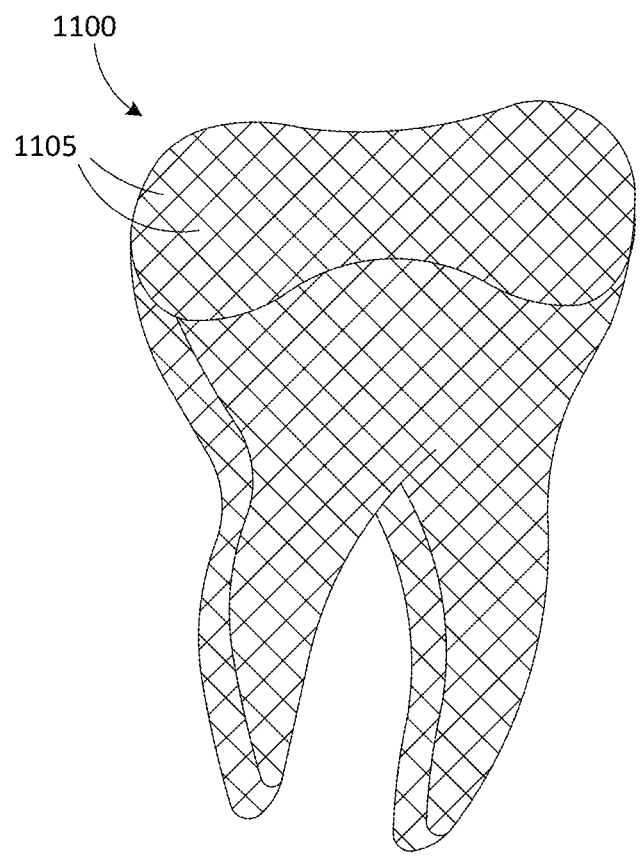
FIG. 11 depicts an exemplary visualization of a three-dimensional digital model of the tooth depicted by FIG. 10.

FIG. 11 depicts an exemplary visualization of a three-dimensional digital model of the tooth depicted by FIG. 10. In FIG. 11, the visualization 1100 of the three-dimensional digital model of the tooth 1000 was constructed from a three-dimensional optical scan of the tooth 1000. In the depicted implementation, the visualized three-dimensional digital model includes a grid comprising mesh cells 1105. In the depicted implementation, mesh cells encompass the entire surface of the tooth. Each mesh cell is individually located and uniquely identified in the three-dimensional digital model. The three-dimensional digital model is created from a set of points in three-dimensional space. In the depicted example, the three-dimensional digital model is based on a three-dimensional scan by the optical scanner 140, depicted by at least FIG. 1. In the depicted example, the three-dimensional digital model represents the surface of the tooth 1000 based on connecting the points from the scan to form the grid of mesh cells that approximates the tooth's shape. Various algorithms are available to one of ordinary skill for creating a model to approximate the tooth's shape. For example, Delaunay triangulation is a geometric technique that constructs 3D tooth surfaces from point cloud data obtained through scans. Delaunay triangulation focuses on point connectivity, while marching cubes extracts surfaces from scalar fields. Marching cubes is a geometric technique for polygonising 3D scalar fields (such as medical images or implicit surfaces) into a mesh of triangles. An implementation may employ Delaunay triangulation or marching cubes, or any other suitable algorithm as a design choice for creating a model to approximate the tooth's shape.

Figure 12:
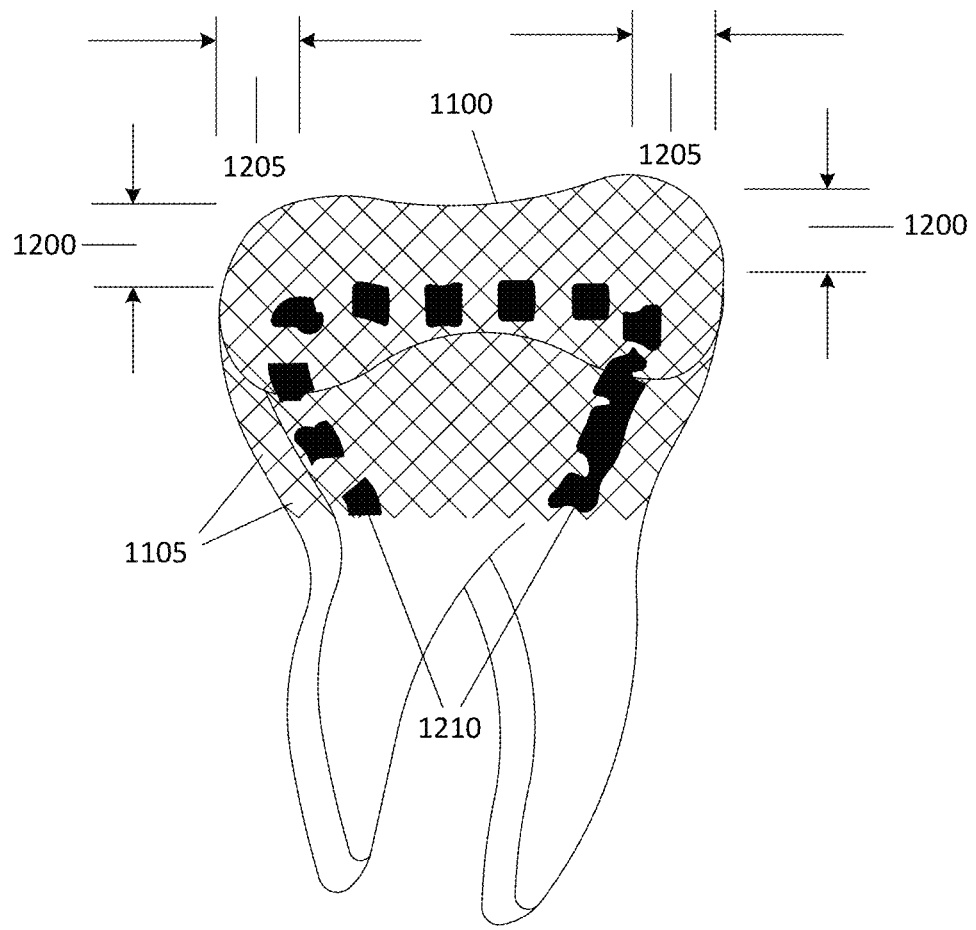
FIG. 12 depicts an exemplary visualization of augmenting a three-dimensional digital model of the tooth depicted by FIG. 10.

FIG. 12 depicts an exemplary visualization of augmenting a three-dimensional digital model of the tooth depicted by FIG. 10. In the implementation depicted by FIG. 12, the visualization 1100 of the three-dimensional digital model of the tooth 1000 is visually presented to the dentist via the user interface display 125, depicted by at least FIG. 1. In the depicted implementation, the dentist creates a reduction plan from the three-dimensional digital model of the tooth. The reduction plan includes axial reduction 1200 (removing excess tooth material vertically) and proximal reduction 1205 (removing material from the sides). In the depicted implementation, the reduction plan includes the reduction depth line 1210. The dentist may specify the reduction depth line 1210 for each mesh cell 1105. The dental robot may remove material from the tooth at each mesh cell location to the depth specified by the reduction depth line 1210.

Figure 13:
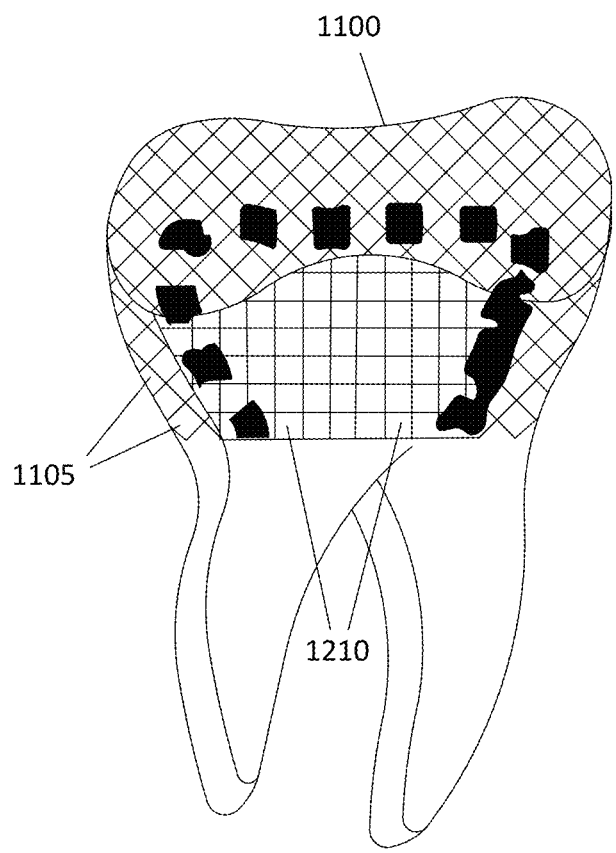
FIG. 13 depicts an exemplary visualization of an augmented three-dimensional digital model of the tooth depicted by FIG. 10.

FIG. 13 depicts an exemplary visualization of an augmented three-dimensional digital model of the tooth depicted by FIG. 10. In FIG. 13, the augmented three-dimensional digital model of the tooth depicted by FIG. 10 is a reduction plan. The reduction plan specifies an amount of material to be removed at each mesh cell 1105. The reduction plan may be a digital copy of the three-dimensional model of the tooth. The digital copy of the three-dimensional model of the tooth may be augmented by adding to the model the amount of material to be removed at each mesh cell 1105. A manipulator arm controller implementing the reduction plan may traverse the model from mesh cell 1105 to mesh cell 1105. The controller may move the manipulator arms to the location in three-dimensional space for the current mesh cell 1105. The controller may activate the reducing tool to remove material from the current mesh cell 1105. The controller may move the manipulator arms to guide the reducing tool to remove material from the tooth at the location specified by the mesh cell 1105. The controller may remove material until reaching the reduction depth line 1210. A dental robot controller reducing a tooth with a reducing tool may use the reduction plan by traversing a list of mesh cells and removing the specified amount of material from the tooth at each point.

Figure 14:
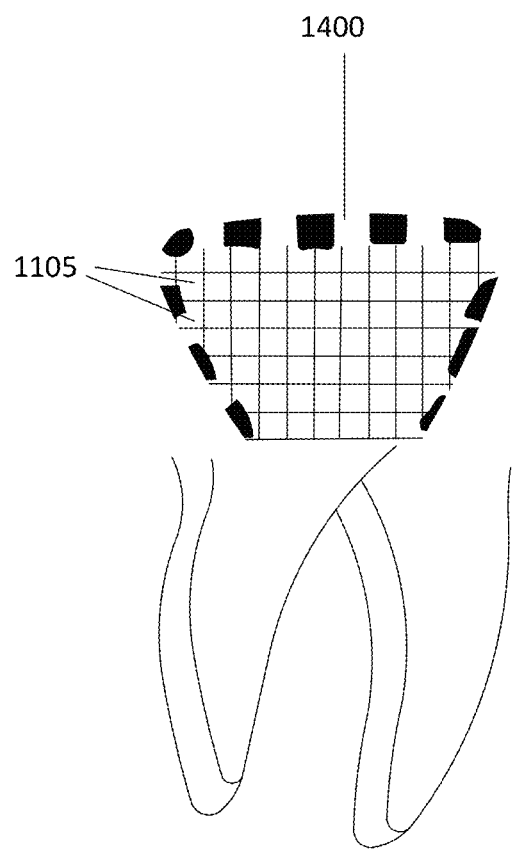
FIG. 14 depicts an exemplary visualization of a three-dimensional digital model of the tooth depicted by FIG. 10 after reduction.

FIG. 14 depicts an exemplary visualization of a three-dimensional digital model of the tooth depicted by FIG. 10 after reduction. In FIG. 14, the depicted three-dimensional digital model 1400 of the reduced tooth is constructed from the optical scan 150, depicted at least by FIG. 1, to use the most accurate representation for forming a crown.

Figure 15:
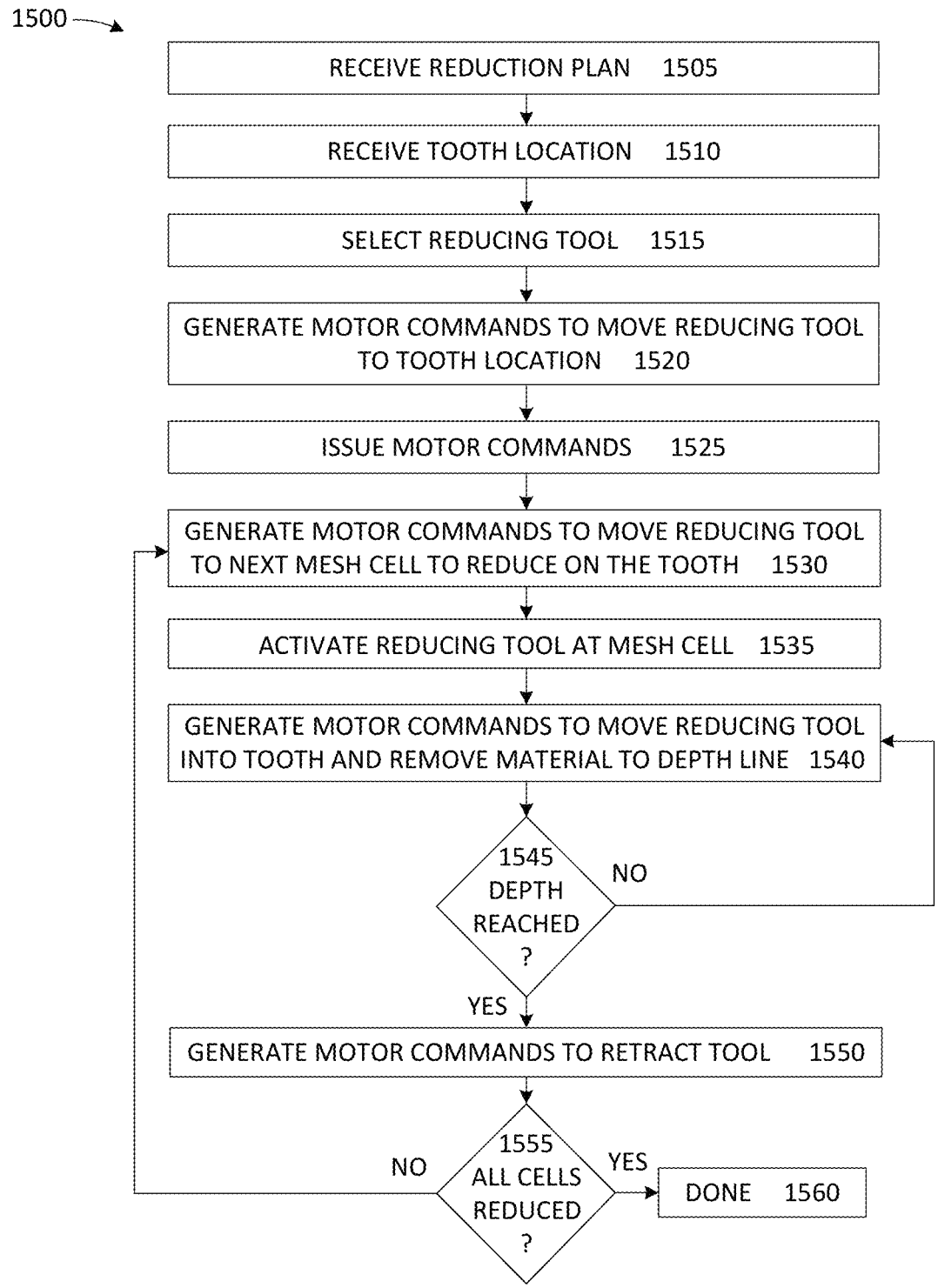
FIG. 15 depicts a process flow of an exemplary dental robot control system moving manipulator arms using a three-dimensional digital reduction plan in an exemplary crown preparation mode.

FIG. 15 depicts a process flow of an exemplary dental robot control system moving manipulator arms using a three-dimensional digital reduction plan in an exemplary crown preparation mode.

In FIG. 15, the depicted method 1500 is given from the perspective of the robotic dentistry engine (RDE) 220 implemented via processor-executable program instructions executing on the dental robot 110 processor 200, depicted in FIG. 2. In some implementations, the RDE 220 may execute as a cloud service communicatively and operatively coupled with system services, hardware resources, or software elements local to and/or external to the dental robot 110. In some designs, the RDE 220 may collaboratively execute both on the processor 200 as a process local to the dental robot 110 and on another processor remote from the dental robot 110.

The depicted method 1500 begins at step 1505 with the processor 200 receiving a reduction plan. The reduction plan may be a digital reduction plan. The reduction plan may be received via a user interface. The reduction plan may be received from a computing device operably coupled with the processor 200.

The method continues at step 1510 with the processor 200 receiving a location of a tooth to be reduced. The processor 200 may derive the location of the tooth from the reduction plan. The reduction plan may comprise an indication of a tooth to be reduced. The tooth to be reduced may be identified in the reduction plan by a number. The indication of the tooth to be reduced may be confirmed using image-based object detection techniques in accordance with what has been disclosed herein with reference to robotic extraction. The reduction plan may comprise an indication of one or more mesh cells located on the tooth. The reduction plan may indicate a predetermined reduction depth for each mesh cell.

The method continues at step 1515 with the processor 200 selecting a reducing tool. The processor 200 may receive a selection of the reducing tool via the user interface.

The method continues at step 1520 with the processor 200 generating motor commands to move the reducing tool to the location of the tooth within the patient's mouth.

The method continues at step 1525 with the processor 200 issuing the motor commands generated by the processor at step 1520.

The method continues at step 1530 with the processor 200 generating motor commands to move the reducing tool to the next mesh cell to be reduced on the tooth.

The method continues at step 1535 with the processor 200 activating the reducing tool to begin removing tooth material at the location of the mesh cell to be reduced on the tooth.

The method continues at step 1540 with the processor 200 generating motor commands to move the activated reducing tool into the tooth toward the tooth interior, while removing tooth material at the location of the mesh cell to a predetermined reduction depth line.

At step 1545 the processor 200 performs a test to determine if enough tooth material has been removed at the location of the mesh cell to reach a predetermined reduction depth specified for the mesh cell by the reduction plan. The processor 200 may determine if enough tooth material has been removed based on comparing sensor data representing the current position of the reducing tool with a starting position or an estimated ending position of the reducing tool. In some implementations, the processor 200 may be configured to advance the reduction tool to the depth line in fractional steps. For example, each fractional step may be a predetermined fraction of the distance from the surface of the unprepared tooth to the depth line. The processor 200 may be configured to pause the reduction tool at each fractional step. During such a pause, the processor 200 may be configured to present the dentist with a visualization of the tooth showing the reduction tool depth overlaid on the user interface display with the depth line. The visualization may show the distance remaining to the depth line. This facilitation may permit the dentist to interrupt the reduction process.

Upon a determination by the processor 200 at step 1545 that enough tooth material has been removed at the location of the mesh cell to reach the predetermined reduction depth, the method continues at step 1550. Upon a determination by the processor 200 at step 1545 that not enough tooth material has been removed at the location of the mesh cell to reach the predetermined reduction depth, the method continues at step 1540.

At step 1550 the processor 200 generates motor commands to retract the reducing tool. The processor 200 issues the motor commands to retract the reducing tool.

At step 1555 the processor 200 performs a test to determine if all mesh cells indicated by the reduction plan have been reduced. Upon a determination by the processor 200 at step 1555 that all mesh cells have been reduced, the method continues to step 1560. Upon a determination by the processor 200 at step 1555 that not all mesh cells have been reduced, the method continues at step 1530.

At step 1560, the method ends.

In some implementations, the method may repeat.

Implementation 1. A method comprising: receiving an initial reduction plan to reduce a tooth, using at least one processor; presenting, to a dentist, the initial reduction plan for approval; upon approval of the initial reduction plan, reducing the tooth according to the approved initial reduction plan, using a reducing tool and the at least one processor; upon rejection, by the dentist, of the initial reduction plan, modifying the initial reduction plan based on input from the dentist; receiving the modified reduction plan to reduce the tooth, using the at least one processor; presenting, to the dentist, the modified reduction plan for approval; and upon approval of the modified reduction plan, reducing the tooth according to the approved modified reduction plan, using the reducing tool and the at least one processor.

Implementation 2. The method of implementation 1, wherein the method further comprises: upon rejection of the modified reduction plan, modifying the modified reduction plan based on input from the dentist; receiving the modified reduction plan to reduce the tooth; and presenting the modified reduction plan to the dentist for approval, using the at least one processor.

Implementation 3. The method of implementation 1, wherein the method further comprises fabricating a crown to fit the reduced tooth, using the at least one processor and a mill guided by a 3d map generated from an optical scan of the reduced tooth.

Implementation 4. The method of implementation 3, wherein the method further comprises sending the 3d map of the reduced tooth to the mill, using the at least one processor.

Implementation 5. The method of implementation 1, wherein the method further comprises generating a 3d model of the tooth based on an optical scan of the tooth before reduction, using the at least one processor.

Implementation 6. The method of implementation 1, wherein receiving the initial reduction plan further comprises receiving the initial reduction plan from the dentist, using the at least one processor.

Implementation 7. The method of implementation 6, wherein the initial reduction plan is determined by the dentist using a 3d-cad system and a 3d scan of the tooth before reduction.

Implementation 8. The method of implementation 1, wherein receiving the initial reduction plan further comprises the initial reduction plan determined by the at least one processor using a 3d scan of the tooth before reduction.

Implementation 9. A method comprising: receiving a scanned image of a tooth and a surrounding area, using at least one processor; presenting the scanned image of the tooth to a dentist, using the at least one processor and a user interface; and upon receiving, from the dentist via the user interface, confirmation that a correct tooth is targeted for extraction: grabbing a neck of the tooth, using the at least one processor and forceps; determining if the tooth is decayed based on analysis of the scanned image of the tooth by a trained decay classification machine learning model, using the at least one processor; in response to determining the tooth is decayed: presenting the scanned image of the tooth to the dentist using the at least one processor and the user interface; determining if the tooth is completely decayed based on analysis of the scanned image of the tooth by a trained decay extent determination machine learning model, using the at least one processor; in response to determining the tooth is completely decayed: receiving an extraction plan created by the dentist for the completely decayed tooth, using the at least one processor and the user interface, wherein the extraction plan comprises sectioning roots of the completely decayed tooth; and sectioning the roots of the completely decayed tooth, using the at least one processor and a surgical handpiece; and in response to determining the tooth is not completely decayed: presenting the scanned image of the tooth to the dentist using the at least one processor and the user interface, for identifying a firm surface location on the tooth; and in response to receiving identification of a firm surface location on the tooth, grabbing a neck of the tooth at the firm surface location on the tooth, using the at least one processor and forceps; severing a periodontal ligament and luxating the tooth, using the at least one processor and an elevator/luxator; and extracting the tooth, using the at least one processor and the forceps.

Implementation 10. The method of implementation 9, wherein after extracting the tooth, the method further comprises receiving a scanned image of the area surrounding the extracted tooth, using the at least one processor.

Implementation 11. The method of implementation 10, wherein the method further comprises determining if there is bleeding from the area surrounding the extracted tooth. The dentist may determine if there is bleeding from the area surrounding the extracted tooth. In a case wherein the dentist determines there is bleeding, the dentist may indicate the location or site of the bleeding using the user interface to the dental robot. For example, the dentist may indicate bleeding from the socket where the tooth was extracted. The dental robot may be programmed and configured to implement one or more actions to stop the bleeding. For example the dental robot may be configured to use a laser to stop the bleeding, at the location or site of the bleeding indicated on the user interface by the dentist. The dental robot may be programmed and configured to determine if there is bleeding from the area surrounding the extracted tooth, based on analysis of the scanned image using the at least one processor and image processing techniques.

Implementation 12. The method of implementation 10, wherein the method further comprises in response to determining there is bleeding, stopping the bleeding, using the at least one processor and a laser.

Implementation 13. The method of implementation 9, wherein the method further comprises injecting an anesthetic, using the at least one processor and a syringe.

Implementation 14. The method of implementation 13, wherein the anesthetic further comprises Novocaine®.

Implementation 15. The method of implementation 9, wherein receiving the scanned image further comprises receiving an image resulting from an optical scan, an X-ray or a CT scan.

Implementation 16. The method of implementation 9, wherein the method further comprises presenting the scanned image of the tooth to the dentist with an indication that an image-based object detection algorithm has determined the depicted tooth is the correct tooth targeted for extraction.

Implementation 17. The method of implementation 9, wherein the trained decay classification machine learning model further comprises at least one Convolutional Neural Network (CNN) trained with a training data set comprising labeled ground truth images depicting decayed or healthy teeth, and wherein the decay classification machine learning model is trained to classify an image of the tooth as depicting at least some decay or no decay determined as a function of an input image.

Implementation 18. The method of implementation 9, wherein the trained decay extent determination machine learning model further comprises at least one Convolutional Neural Network (CNN) trained with a training data set comprising labeled ground truth images subdivided into a mesh of cell regions labeled as decayed or healthy, wherein the training data set further comprises a percentage value of grid cells for each tooth which show decayed tooth material, and wherein the decay extent determination machine learning model is trained to determine a percentage of grid cells showing decayed tooth material as a function of an input image.

Implementation 19. An article of manufacture comprising a non-transitory computer readable storage medium retrievably storing processor executable instructions configured to cause a robotic dentistry system to perform crown preparation operations comprising: receive an initial reduction plan to reduce a tooth, using at least one processor; present, to a dentist, the initial reduction plan for approval; upon approval of the initial reduction plan, reduce the tooth according to the approved initial reduction plan, using a reducing tool and the at least one processor; upon rejection, by the dentist, of the initial reduction plan, modify the initial reduction plan based on input from the dentist; receive the modified reduction plan to reduce the tooth, using the at least one processor; present, to the dentist, the modified reduction plan for approval; and upon approval of the modified reduction plan, reduce the tooth according to the approved modified reduction plan, using the reducing tool and the at least one processor.

Implementation 20. An article of manufacture comprising a non-transitory computer readable storage medium retrievably storing processor executable instructions configured to cause a robotic dentistry system to perform tooth extraction operations comprising: receive a scanned image of a tooth and a surrounding area, using at least one processor; present the scanned image of the tooth to a dentist, using the at least one processor and a user interface; upon receiving confirmation from the dentist via the user interface that the tooth targeted for extraction is correct: sever a periodontal ligament and luxate the tooth, using the at least one processor and an elevator/luxator; determine if the tooth is decayed based on analysis of the scanned image of the tooth, using the at least one processor; in response to determining the tooth is decayed, grab a neck of the tooth, using the at least one processor and forceps; in response to determining the tooth is not decayed, grab a firm surface of the tooth above the neck of the tooth, using the at least one processor and the forceps; and extract the tooth, using the at least one processor and the forceps.

Implementation 21. A method comprising: receiving a scanned image of a tooth and a surrounding area, using at least one processor; presenting the scanned image of the tooth to a dentist, using the at least one processor and a user interface; and upon receiving, from the dentist via the user interface, confirmation that a correct tooth is targeted for extraction: determining if the tooth is decayed based on analysis of the scanned image of the tooth by a trained decay classification machine learning model, using the at least one processor; in response to determining the tooth is not decayed: grabbing a neck of the tooth, using the at least one processor and forceps; in response to determining the tooth is decayed: presenting the scanned image of the tooth to the dentist using the at least one processor and the user interface; determining if the tooth is completely decayed based on analysis of the scanned image of the tooth by a trained decay extent determination machine learning model, using the at least one processor; in response to determining the tooth is completely decayed: receiving an extraction plan created by the dentist for the completely decayed tooth, using the at least one processor and the user interface, wherein the extraction plan comprises sectioning roots of the completely decayed tooth; and sectioning the roots of the completely decayed tooth, using the at least one processor and a surgical handpiece; and in response to determining the tooth is not completely decayed: presenting the scanned image of the tooth to the dentist using the at least one processor and the user interface, for identifying a firm surface location on the tooth; and in response to receiving identification of a firm surface location on the tooth, grabbing a neck of the tooth at the firm surface location on the tooth, using the at least one processor and forceps; severing a periodontal ligament and luxating the tooth, using the at least one processor and an elevator/luxator; and extracting the tooth, using the at least one processor and the forceps.

Implementation 22. The method of implementation 21, wherein after extracting the tooth, the method further comprises receiving a scanned image of the area surrounding the extracted tooth, using the at least one processor.

Implementation 23. The method of implementation 22, wherein the method further comprises determining if there is bleeding from the area surrounding the extracted tooth, based on analysis of the scanned image, using the at least one processor.

Implementation 24. The method of implementation 22, wherein the method further comprises in response to determining there is bleeding, stopping the bleeding, using the at least one processor and a laser.

Implementation 25. The method of implementation 21, wherein the method further comprises injecting an anesthetic, using the at least one processor and a syringe.

Implementation 26. The method of implementation 25, wherein the anesthetic further comprises Novocaine®.

Implementation 27. The method of implementation 21, wherein receiving the scanned image further comprises receiving an image resulting from an optical scan, an X-ray or a CT scan.

Implementation 28. The method of implementation 21, wherein the method further comprises presenting the scanned image depicting the tooth to the dentist with an indication that an image-based object detection algorithm has determined the depicted tooth is the correct tooth targeted for extraction.

Implementation 29. The method of implementation 21, wherein the trained decay classification machine learning model further comprises at least one Convolutional Neural Network (CNN).

Implementation 30. The method of implementation 29, wherein the at least one CNN is trained with a training data set comprising labeled ground truth images depicting decayed or healthy teeth.

Implementation 31. The method of implementation 29, and wherein the at least one CNN is trained to classify an image of the tooth as depicting at least some decay or no decay determined as a function of an input image.

Implementation 32. The method of implementation 31, wherein the trained decay extent determination machine learning model further comprises at least one Convolutional Neural Network (CNN) trained with a training data set comprising ground truth images subdivided into a mesh of cell regions.

Implementation 33. The method of implementation 32, wherein the ground truth images are labeled as decayed or healthy.

Implementation 34. The method of implementation 32, wherein each ground truth image of an individual tooth is labeled with a percentage value of grid cells which show decayed tooth material for the individual tooth.

Implementation 35. The method of implementation 32, wherein the decay extent determination machine learning model is trained to determine a percentage of grid cells showing decayed tooth material as a function of an input image.

Implementation 36. The method of implementation 21, wherein the method further comprises selecting surface locations that are not decayed on opposing sides of the tooth, by the at least one processor using the trained decay extent determination machine learning model.

Implementation 37. The method of implementation 36, wherein the method further comprises applying gripping force to the selecting surface locations, using the at least one processor.

Implementation 38. The method of implementation 21, wherein the method further comprises determining if a patient is bleeding from an extraction site based on comparing color histograms of images of the extraction site before extraction and after extraction.

Implementation 39. The method of implementation 21, wherein the method further comprises determining if a patient is bleeding from an extraction site based on an optical flow algorithm analyzing a video of the extraction site captured after extraction.

Implementation 40. An article of manufacture comprising a non-transitory computer readable storage medium retrievably storing processor executable instructions configured to cause a robotic dentistry system to perform tooth extraction operations comprising: receive a scanned image of a tooth and a surrounding area, using at least one processor; present the scanned image of the tooth to a dentist, using the at least one processor and a user interface; upon receiving confirmation from the dentist via the user interface that the tooth targeted for extraction is correct: determine if the tooth is decayed based on analysis of the scanned image of the tooth by a trained decay classification machine learning model, using the at least one processor; in response to determining the tooth is not decayed, grab a neck of the tooth, using the at least one processor and forceps; in response to determining the tooth is decayed, grab a surface of the tooth above the neck of the tooth, using the at least one processor and the forceps; sever a periodontal ligament and luxate the tooth, using the at least one processor and an elevator/luxator; and extract the tooth, using the at least one processor and the forceps.

Implementation 41. An apparatus comprising: a tooth extraction device configured with a plurality of end effectors and a controller, wherein the plurality of end effectors comprise at least one forceps configured to grip and extract an individual tooth to be extracted from a patient's jaw with variable force and at least one elevator configured to loosen the tooth by cutting ligaments securing the tooth in the patient's jaw, wherein the controller is operably coupled with the tooth extraction device, and wherein the controller is configured to cause the apparatus to perform operations comprising: determine if the tooth is loose enough to be extracted with a predetermined minimum extraction force applied by the forceps, comprising using the predetermined minimum extraction force to attempt to move the tooth with the forceps while capturing accelerometer data from the forceps and comparing the captured accelerometer data to predetermined extraction threshold accelerometer data, the captured accelerometer data representing movement of the tooth in response to the predetermined minimum extraction force applied to the tooth by the forceps; in response to determining the tooth is not loose enough to be extracted, loosen the tooth, using a predetermined minimum loosening force by a first elevator of the at least one elevator; attempt to extract the loosened tooth, using the forceps with an extraction force adjusted to the predetermined minimum extraction force; determine if the tooth has been extracted, based on accelerometer data from the forceps; and in response to determining the tooth has not been extracted, iteratively and until determining the tooth has been extracted, increase the extraction force by a predetermined extraction force increment and attempt to extract the loosened tooth, using the forceps with an extraction force adjusted to the increased extraction force.

Implementation 42. The apparatus of implementation 41, wherein the apparatus further comprises a camera configured in at least one end effector, wherein the camera is operably coupled with the controller and the controller is further configured to cause the apparatus to perform operations further comprising capture an image of a location of the tooth, using the camera.

Implementation 43. The apparatus of implementation 42, wherein the operations performed by the apparatus further comprise: determine if the tooth has been extracted based on analyzing the captured image.

Implementation 44. The apparatus of implementation 42, wherein the operations performed by the apparatus further comprise: determine if the tooth is a whole tooth based on analyzing the captured image; and upon a determination that the tooth is not a whole tooth, halt the operations performed by the apparatus.

Implementation 45. The apparatus of implementation 42, wherein the operations performed by the apparatus further comprise: determine if the tooth is an exposed tooth based on analyzing the captured image; and upon a determination that the tooth is not an exposed tooth, halt the operations performed by the apparatus.

Implementation 46. The apparatus of implementation 41, wherein the controller is further configured to cause the apparatus to perform further operations comprising: determine if the ligaments securing the tooth have been cut, based on comparing captured accelerometer data from the forceps to the predetermined extraction threshold accelerometer data; and upon a determination the ligaments have been cut, lifting out the tooth with a second elevator of the at least one elevator.

Implementation 47. The apparatus of implementation 41, wherein the controller is further configured to cause the apparatus to perform further operations comprising using imaging, sensors and end effectors with computer vision and artificial intelligence (AI) techniques to evaluate tooth condition and tooth readiness for crown placement.

Implementation 48. The apparatus of implementation 47, wherein the controller is further configured to cause the apparatus to perform further operations comprising evaluating tooth size and condition, considering factors like decay, damage, or infection, using probes, sensors and images as input to the AI.

Implementation 49. The apparatus of implementation 47, wherein the controller is further configured to cause the apparatus to perform further operations comprising assessing a damaged tooth and determining if a crown is necessary.

Implementation 50. The apparatus of implementation 47, wherein the controller is further configured to cause the apparatus to perform further operations comprising using end effectors such as ablation tools to remove any existing decay guided by real time computer vision and a three-dimensional digital map of the tooth and a patient's oral cavity scanned by an imaging sensor.

Implementation 51. The apparatus of implementation 47, wherein the controller is further configured to cause the apparatus to perform further operations comprising removing tooth material using one or more end effectors to shape the tooth to accommodate the crown.

Implementation 52. The apparatus of implementation 47, wherein the controller is further configured to cause the apparatus to perform further operations comprising making dental impressions using digital scans or traditional molds to capture an exact shape of a prepared tooth.

Implementation 53. The apparatus of implementation 47, wherein the controller is further configured to cause the apparatus to perform further operations comprising directing a three-dimensional milling machine to fabricate the crown using a digital model of a patient's oral cavity.

Implementation 54. The apparatus of implementation 53, wherein the controller is further configured to cause the apparatus to perform further operations comprising interactively collaborating with the milling machine and a human dentist via a high-resolution touch-screen interactive display using a digital map of the patient's oral cavity scanned by a camera to guide crown preparation.

Implementation 55. The apparatus of implementation 53, wherein the controller is further configured to cause the apparatus to perform further operations comprising iteratively removing tooth material to resize a tooth stump or post to accept the crown while the crown is being milled by the milling machine, in a communication and control feedback loop comparing a size of the stump or post measured by an optical scan to a digital model of an interior of the crown being prepared by the milling machine.

Implementation 56. The apparatus of implementation 53, wherein the controller is further configured to cause the apparatus to perform further operations comprising placing the crown onto the tooth with cement or a suitable dental adhesive.

Although various implementations have been described with reference to the Drawings, other implementations are possible. For example, the dental robot may be configured to implement safety measures. Such safety measures may comprise collision avoidance, based on sensor information. The control system may use sensors to detect obstacles and prevent collisions, while algorithms like RRT (Rapidly Exploring Random Tree) may ensure collision-free trajectories. Additionally, clearance validation may provide a safe distance between the tool-head and adjacent teeth.

Exemplary tooth preparation workflow may comprise axial reduction (removing excess tooth material vertically), proximal reduction (removing material from the sides), and milling the crown based on a digital milling plan. The digital milling plan may be generated by the robot, or the dentist.

Some key aspects of the presently disclosed robotic dentistry technology may comprise advanced use of sensors, such as accelerometers and proximity detectors to provide real-time feedback on acceleration, vibration, and detection of nearby objects or surfaces. The disclosed robotic dentistry technology may provide precise movement using a 6-DOF manipulator with stepper motors, permitting more precise crown preparation. In some examples, motion control algorithms may use inverse kinematics, collision avoidance, and path planning to ensure efficient and safe operation. An implementation of the presently disclosed robotic dentistry technology permits collaboration between the human dentist and the dental robot, allowing for dentist control of the treatment procedure based on input from the dentist.

A method implemented by an exemplary dental robot to select an extraction technique based on determining the extent decay in a tooth targeted for extraction may comprise: locating and identifying a tooth targeted for extraction based on analysis of an image of the patient's teeth; determining if the tooth is decayed based on analysis of an image of the tooth; in response to determining the tooth is not decayed, guiding the dental robot to extract the tooth using forceps; in response to determining the tooth has at least some decay, determining if the tooth is completely decayed based on analysis of the image of the tooth; in response to determining the tooth is not completely decayed, guiding the dental robot to grab the tooth by a solid surface of the tooth using forceps and extracting the tooth using the forceps; and in response to determining the tooth is completely decayed, guiding the dental robot (optionally in collaboration with the dentist) to sever the roots of the completely decayed tooth before extracting the tooth using the forceps. The processor may determine if a tooth is generally decayed or the processor may determine the extent or degree of decay in a tooth, using one or more trained machine learning models configured to determine decay or extent of decay as a function of one or more image.

An exemplary dental robot may execute a decay extent assessment algorithm to determine the extent of decay in a tooth classified as decayed by the decay detection machine learning model. The decay extent assessment algorithm may segment an image depicting at least one tooth into a plurality of grid cells forming a mesh of grid cells subsuming the entire surface of the tooth. The decay extent assessment algorithm may include a decay detection convolutional neural network trained on ground truth images each depicting a tooth having decay or a tooth not having decay. The dental robot may execute the decay extent assessment algorithm using the decay detection convolutional neural network to classify each grid cell of the plurality of grid cells as having decay or not having decay. The decay extent assessment algorithm may comprise determining the number of grid cells in a tooth that were classified by the decay detection convolutional neural network as having decay. The decay extent assessment algorithm may comprise determining a percentage of the number of grid cells in the tooth as having decay. The decay extent assessment algorithm may comprise comparing the percentage of the number of grid cells in the tooth as having decay to a predetermined threshold, to determine if the tooth is completely decayed based on the comparison. For example, in response to determining the tooth is completely decayed, the selected extraction technique may comprise controlling the dental robot to section roots of the completely decayed tooth before extracting the tooth using forceps. For example, in response to determining the tooth is not completely decayed, the selected extraction technique may comprise identifying surface locations that are not decayed on opposing sides of the tooth determined as a function of the image, and grabbing a neck of the tooth at the firm surface locations on the tooth, using the at least one processor and forceps.

An exemplary dental robot is a sophisticated device designed to perform dental procedures, including tooth extraction and crown preparation. The robot is equipped with advanced image processing systems enhanced by machine learning and artificial intelligence. An exemplary dental robot's electronic design may comprise multiple processors (CPUs) running in parallel to ensure efficient data processing. A central processing unit (CPU) may manage the overall operation of the robot, while dedicated processors may be assigned to perform specific tasks such as image processing, machine learning algorithms, and motor control. Power supply units (PSUs) may provide stable power to all electronic components. An exemplary dental robot's mechanical design may comprise of a sturdy and precision-crafted robotic arm with multiple degrees of freedom, allowing for precise movement and positioning in the oral cavity. The robotic arm may be composed of a series of interconnected links connected by high-precision actuators (joints) that enable smooth and controlled motion. A suction system may be integrated to maintain a stable environment within the oral cavity during procedures.

An exemplary dental robot's image processing system may be configured to receive multiple types of scans, including optical, X-ray, CT, or other types of 3D scans, and segment them into individual teeth using segmentation algorithms. Object detection and identification algorithms may be executed to locate and identify individual teeth in the segmented images, utilizing a numbering system (e.g., Upper Jaw: 1-16, Lower Jaw: 17-32). Ground truth images may be used to train object detection models for tooth recognition.

An exemplary dental robot's robotic arms may be designed to execute precise movements and positioning within the oral cavity. A forceps attachment may be integrated into the robotic arm to allow for grasping and manipulating teeth during procedures. An exemplary dental robot may automatically guide itself to extract teeth using a selected technique based on tooth classification (decayed or not decayed) by a trained machine learning model.

An exemplary dental robot may be configured with software comprising machine learning models (decay detection) that classify teeth as decayed or not decayed, and algorithms for decay extent assessment. Ground truth images may be used to train the decay detection convolutional neural network. The software may be designed to execute in parallel with other processors to ensure efficient data processing. A trained decay detection model may classify teeth as decayed or not decayed based on input images. A decay extent assessment algorithm may determine the extent of decay in a tooth, utilizing a grid cell segmentation approach and a decay detection convolutional neural network. The software may be configured to automatically select an extraction technique (e.g., forceps grip for not completely decayed teeth or sectioning roots for completely decayed teeth) based on the classification and assessment results.

An exemplary dental robot's design may combine advanced image processing, machine learning algorithms, and robotic mechanics to enable precise and efficient tooth extraction procedures. The robot may accurately classify teeth as decayed or not decayed and automatically select an extraction technique based on the assessment results.

An exemplary dental robot may be designed with safety features, such as stable power supply, suction system, and controlled movement. User interfaces and alarms are integrated to alert users of potential risks or malfunctions.

Disclosed herein is an exemplary tooth extraction device configured to use forceps to determine if a tooth is loose enough for extraction, otherwise loosening the tooth using a first elevator, and extracting the loosened tooth using the forceps upon determining the tooth has been loosened enough for extraction. The determination of whether the tooth is loose enough for extraction may be based on accelerometer data received from the forceps. Loosening the tooth may comprise using the first elevator to cut ligaments securing the tooth. Tooth extraction may be aided using a second elevator to lift the tooth upon determining the ligaments are cut, based on captured accelerometer data. Extraction may be halted upon determining the tooth is broken or not exposed, based on an image of the tooth location captured by camera. The device may iteratively increment and compare extraction force and loosening force to threshold forces, until tooth extraction is complete.

According to an aspect of the present disclosure, there is provided an apparatus. The apparatus may comprise a tooth extraction device. The tooth extraction device may be configured with a plurality of end effectors and a controller. The plurality of end effectors may comprise at least one forceps and at least one elevator. The forceps may be configured to grip and extract an individual tooth to be extracted from a patient's jaw with variable force. The elevator may be configured to loosen the tooth by cutting ligaments securing the tooth in the patient's jaw. The controller may be operably coupled with the tooth extraction device.

The controller may be configured to cause the apparatus to perform operations. The operations may comprise determining if the tooth is loose enough to be extracted with a predetermined minimum extraction force applied by the forceps. This determination is made by using the predetermined minimum extraction force to attempt to move the tooth with the forceps. Accelerometer data is captured from the forceps during this attempt and is compared to predetermined extraction threshold accelerometer data. The captured accelerometer data represents movement of the tooth in response to the predetermined minimum extraction force applied to the tooth by the forceps.

In response to determining that the tooth is not loose enough to be extracted, the controller may cause the apparatus to loosen the tooth. This is done using a predetermined minimum loosening force by a first elevator of the at least one elevator. The controller also causes the apparatus to attempt to extract the loosened tooth. This is done using the forceps with an extraction force adjusted to the predetermined minimum extraction force.

The controller may be further configured to determine if the tooth has been extracted. This determination is based on accelerometer data from the forceps. In response to determining that the tooth has not been extracted, the controller may cause the apparatus to iteratively and until determining that the tooth has been extracted, increase the extraction force by a predetermined extraction force increment. The apparatus may then attempt to extract the loosened tooth, using the forceps with an extraction force adjusted to the increased extraction force.

Optionally, the apparatus further comprises a camera. The camera is configured in at least one end effector of the apparatus. The camera is operably coupled with the controller. The controller is further configured to cause the apparatus to perform operations. These operations further comprise capturing an image of a location of the tooth, using the camera.

Optionally, the apparatus, as described above, further comprises operations. These operations are performed by the apparatus and comprise determining if the tooth has been extracted. The determination is based on analyzing the captured image.

Optionally, the apparatus, as described above, further comprises operations performed by the apparatus. These operations include determining if the tooth is a whole tooth. This determination is based on analyzing the captured image. Additionally, upon a determination that the tooth is not a whole tooth, the apparatus halts the operations performed by the apparatus.

Optionally, the apparatus, as described above, further comprises operations performed by the apparatus. These operations include determining if the tooth is an exposed tooth. This determination is based on analyzing the captured image. Additionally, upon a determination that the tooth is not an exposed tooth, the apparatus halts the operations performed by the apparatus.

Optionally, the apparatus comprises a controller. The controller is configured to cause the apparatus to perform further operations. One of these operations is to determine if the ligaments securing the tooth have been cut. This determination is based on comparing captured accelerometer data from the forceps to the predetermined extraction threshold accelerometer data.

Additionally, upon a determination that the ligaments have been cut, the controller may be configured to cause the apparatus to lift out the tooth. The lifting out of the tooth is performed with a second elevator of the at least one elevator.

Optionally, the apparatus as described above further comprises a controller. The controller is configured to cause the apparatus to perform additional operations. These operations comprise using imaging, sensors, and end effectors. The controller also utilizes computer vision and artificial intelligence (AI) techniques. The purpose of these techniques is to evaluate tooth condition and tooth readiness for crown placement.

Optionally, the apparatus, as described above, comprises a controller. The controller is configured to cause the apparatus to perform further operations. These operations comprise evaluating the tooth's size and condition. The evaluation takes into consideration factors such as decay, damage, or infection. The controller utilizes probes, sensors, and images as input to an artificial intelligence system.

Optionally, the apparatus, as described above, comprises a controller. The controller is configured to cause the apparatus to perform further operations. These operations comprise assessing the damaged tooth. Additionally, the controller is configured to determine if a crown is necessary.

Optionally, the apparatus, as described above, comprises a controller. The controller is configured to cause the apparatus to perform further operations. These operations comprise using end effectors, such as ablation tools. The purpose of these tools is to remove existing enamel or decay. The removal of enamel or decay is guided by real-time computer vision. Additionally, the removal process is guided by a three-dimensional digital map of the tooth and the patient's oral cavity. This map is scanned by an imaging sensor.

Optionally, the apparatus, as described above, comprises a controller. The controller is configured to cause the apparatus to perform further operations. These operations comprise removing tooth material. The removal of tooth material is performed using one or more end effectors. The purpose of this removal is to shape the tooth in a manner that accommodates the crown.

Optionally, the apparatus, as described above, comprises a controller. The controller is configured to cause the apparatus to perform further operations. These operations comprise making dental impressions. The dental impressions are made using either digital scans or traditional molds. The purpose of these dental impressions is to capture the exact shape of the prepared tooth.

Optionally, the apparatus, as described above, comprises a controller. The controller is configured to cause the apparatus to perform further operations. These further operations comprise directing a three-dimensional milling machine. The direction is to fabricate the crown. The fabrication of the crown is performed using a digital model of the patient's oral cavity.

Optionally, the apparatus comprises a controller. The controller is configured to cause the apparatus to perform further operations. These operations comprise interactively collaborating with the milling machine and the human dentist. The interaction takes place via a high-resolution touch-screen interactive display. The display uses a digital map of the patient's oral cavity. The digital map is scanned by a camera. The camera is used to guide the crown preparation.

Optionally, the apparatus, as described above, comprises a controller. The controller is configured to cause the apparatus to perform further operations. These operations comprise iteratively removing tooth material to resize the tooth stump or post to accept the crown. This resizing operation occurs while the crown is being milled by the milling machine.

Additionally, the controller may operate in a communication and control feedback loop. In this feedback loop, the size of the stump or post may be compared to a digital model of the interior of the crown. The size of the stump or post may be measured by an optical scan.

Optionally, the apparatus, as described above, may comprise a controller. The controller may be configured to cause the apparatus to perform further operations. These operations may comprise placing the crown onto the tooth. The controller may be configured to cause the apparatus to perform this operation with the use of cement or a suitable dental adhesive.

The present invention disclosure comprises a tooth extraction device. This device may be equipped with multiple end effectors, including at least one forceps and one elevator, and a controller. The forceps may be designed to grip and extract a tooth from a patient's jaw with variable force, while the elevator is used to loosen the tooth by severing the ligaments that hold it in place.

The controller, which may be operatively connected to the tooth extraction device, may direct the device to perform a series of operations. Initially, the controller may determine if the tooth is loose enough for extraction by applying a predetermined minimum extraction force with the forceps. This determination may be based on accelerometer data captured from the forceps during this attempt. The data, which represents the movement of the tooth in response to the applied force, may be compared to a predetermined extraction threshold.

If the tooth is not sufficiently loose for extraction, a first elevator from the set of elevators may be used to further loosen it using a predetermined minimum loosening force. Once loosened, an attempt may be made to extract it using the forceps adjusted to the predetermined minimum extraction force.

The controller may determine if the tooth has been successfully extracted based on accelerometer data from the forceps. If not, the controller may increases the extraction force incrementally until successful extraction is achieved. The device may then attempt to extract the loosened tooth using the forceps adjusted to this increased extraction force.

This invention disclosure also introduces an exemplary dental robot configured for tooth extraction. It uses imaging, sensors and end effectors along with computer vision and artificial intelligence (AI) techniques to assess and diagnose tooth condition and carry out tooth extraction. The robot may evaluate factors such as decay, damage or infection using probes, sensors and images as input to its AI system. X-rays may be taken for assessing root structure and surrounding bone.

The dental robot may use dental forceps to determine if the tooth is loose enough for extraction. If not, it may use a dental elevator to gently loosen the tooth by cutting the periodontal ligaments. Once adequately loosened, the robot may use forceps to extract the tooth. In complex cases, a second elevator may be used to further lift the tooth.

The dental robot can provide real-time graphic visualization of the extraction procedure on a high-resolution touch-screen interactive display using a digital map of the patient's oral cavity scanned by a camera. It can also pause the extraction procedure and request human intervention when unexpected conditions are detected based on sensors such as accelerometers or cameras.

The invention disclosure also includes an exemplary dental robot configured for crown preparation. It may use imaging, sensors and end effectors along with computer vision and AI techniques to evaluate tooth condition and readiness for crown placement. The robot may assess the damaged tooth and determines if a crown is necessary. It may use end effectors such as ablation tools to remove any existing decay guided by real-time computer vision and a three-dimensional digital map of the tooth and the patient's oral cavity scanned by an imaging sensor.

The crown preparation dental robot may make dental impressions using digital scans or traditional molds to capture the exact shape of the prepared tooth. The impression may serve as a digital model for directing a three-dimensional milling machine to fabricate the crown. The robot may interact with the milling machine and the dentist via a high-resolution touch-screen interactive display using a digital map of the patient's oral cavity scanned by a camera.

The crown preparation dental robot may iteratively remove tooth material to resize the tooth stump or post to accept the crown while it is being milled by the milling machine. It may place the crown onto the tooth with cement or a suitable dental adhesive. The robot may employ digital scanning and 3D modeling using an optical scanner to create a three-dimensional digital model of the tooth. Real-time imaging may help control a dental ablation device (such as a laser) to precisely reduce the tooth to the desired size for crown placement. The robot may control an in-office milling machine configured to mill a ceramic block to create the customized crown, which is then cemented onto the tooth.

The second elevator may be designed to provide a different method of loosening the tooth by applying ultrasonic vibrations to the tooth, thereby further weakening the ligaments securing the tooth in the patient's jaw. The ultrasonic vibrations can help to break down the periodontal ligaments more effectively, making the extraction process smoother and less traumatic for the patient.

For example, the controller of the apparatus can be programmed to first attempt to loosen the tooth using the first elevator with the predetermined minimum loosening force. If the tooth is not sufficiently loosened for extraction, the controller can then activate the second elevator to apply ultrasonic vibrations to the tooth. Accelerometer data can be collected during this process to monitor the response of the tooth to the ultrasonic vibrations and determine the effectiveness of this loosening method.

Furthermore, the tooth extraction device may include a feedback mechanism that provides real-time data to the controller regarding the resistance encountered during the extraction process. This feedback mechanism can be in the form of a force sensor integrated into the forceps, which continuously measures the force applied during the extraction attempt. The controller can use this data to adjust the extraction force incrementally, ensuring that the optimal force is applied to extract the tooth without causing unnecessary trauma to the surrounding tissues.

Additionally, the tooth extraction device may feature a safety mechanism that automatically stops the extraction process if excessive force is detected, preventing potential damage to the patient's jaw or surrounding teeth. The controller can be programmed to analyze the force data in real-time and trigger an emergency stop if the force exceeds a predetermined threshold, thereby ensuring patient safety during the procedure.

In another alternative embodiment, the tooth extraction device could be equipped with a suction mechanism to remove any blood or debris from the extraction site during the procedure. This can help to improve visibility for the dentist and facilitate a smoother extraction process. The suction mechanism can be activated automatically when the extraction process begins and deactivated once the tooth has been successfully extracted.

Moreover, the tooth extraction device may be designed to be compatible with different types of end effectors, allowing for customization based on the specific needs of the patient or the complexity of the extraction procedure. For instance, the device could be equipped with specialized end effectors for extracting wisdom teeth or teeth with curved roots, providing versatility and efficiency in various clinical scenarios.

The apparatus, as described above, further may comprise a camera. The camera is configured in at least one end effector of the apparatus. The camera is operably coupled with the controller of the apparatus. The controller is further configured to cause the apparatus to perform operations. These operations further comprise capturing an image of a location of the tooth. The camera is used for this image capture operation.

The camera may utilize advanced imaging technologies such as autofocus, image stabilization, and macro capabilities to ensure clear and precise images are obtained.

For example, the camera may be equipped with a zoom function that allows the user to magnify specific areas of the tooth for a closer inspection. This can be particularly useful when identifying small cracks, cavities, or other imperfections that may not be easily visible to the naked eye.

Additionally, the camera may have built-in LED lights or infrared capabilities to improve visibility in low-light conditions within the oral cavity. This ensures that high-quality images can be captured regardless of the lighting environment, enabling accurate diagnosis and treatment planning.

Furthermore, the controller of the apparatus may be programmed with image processing algorithms that analyze the captured images in real-time. These algorithms can detect common dental issues such as decay, plaque buildup, or gum inflammation, providing valuable insights to the user during the dental examination.

Alternatively, the camera may be a 3D imaging camera capable of creating detailed three-dimensional models of the tooth structure. By capturing multiple images from different angles, the camera can reconstruct a digital replica of the tooth, allowing for precise measurements and virtual simulations of various dental procedures.

Moreover, the camera may be equipped with wireless connectivity options, enabling the captured images to be instantly transferred to a computer or mobile device for further analysis or consultation with other dental professionals. This seamless integration of imaging technology enhances communication and collaboration in the dental practice, ultimately leading to improved patient care.

The apparatus, as described above, further may comprise operations. These operations include determining if the tooth has been extracted. The determination may be based on analyzing the captured image, or receiving input from the dentist.

The captured images may then be analyzed by the controller to determine if the tooth has been successfully extracted.

For example, the controller may utilize image processing algorithms to compare the images of the tooth pre and post-procedure. By analyzing factors such as the presence of the entire tooth structure, changes in surrounding tissues, and the absence of the targeted tooth, the controller can accurately determine if the tooth extraction was completed.

Alternatively, the camera may also be used to capture real-time video footage during the extraction process. This live feed can provide valuable insights to the dentist and the controller, allowing them to monitor the procedure and make real-time decisions based on the visual feedback.

Furthermore, the camera can be equipped with additional features such as zoom capabilities, adjustable focus settings, and image enhancement filters to ensure optimal image quality for accurate analysis. The controller may also be programmed to store the captured images for future reference or analysis, providing a comprehensive record of the dental procedure.

The apparatus, as described above, further may comprise operations that involve determining if the tooth is a whole tooth. This determination is based on analyzing the captured image. In addition, the apparatus also may include a feature where, upon a determination that the tooth is not a whole tooth, the operations performed by the apparatus are halted.

These images may then be processed by the controller using image recognition algorithms to determine if the tooth is complete or if there are any missing parts. For example, the controller may analyze the image to identify any cracks, fractures, or missing sections in the tooth structure.

If the analysis indicates that the tooth is complete, the apparatus may continue with the intended dental procedure. However, if the controller determines that the tooth is not whole based on the captured image, the apparatus may automatically halt the ongoing operations. This feature ensures that the apparatus does not proceed with a procedure on a compromised tooth, which could lead to further damage or complications.

In an alternative embodiment, the camera may also be equipped with additional features such as depth perception capabilities or infrared imaging. Depth perception can provide more detailed information about the three-dimensional structure of the tooth, allowing for a more accurate assessment of its integrity. Infrared imaging can be used to detect hidden issues such as cavities or internal damage that may not be visible in standard visible light images.

Furthermore, the apparatus may include a user interface that displays the captured images in real-time, allowing the dental practitioner to visually inspect the tooth before proceeding with any treatment. This real-time feedback can help the practitioner make informed decisions about the best course of action based on the condition of the tooth as shown in the images.

The apparatus, as described above, may further comprise operations that involve determining if the tooth is an exposed tooth. This determination is based on analyzing the captured image. In addition, the apparatus also may include a feature where, upon a determination that the tooth is not an exposed tooth, the operations performed by the apparatus are halted.

The image analysis involves assessing various characteristics such as color, texture, shape, and size to determine if the tooth is exposed or not. For example, the apparatus may be programmed to recognize specific features indicative of an exposed tooth, such as the presence of enamel or the visibility of the tooth surface.

If the analysis indicates that the tooth is not exposed, the controller of the apparatus may be designed to automatically halt the ongoing operations. This feature ensures that the apparatus does not continue with any procedures that are intended for exposed teeth, thereby preventing any unnecessary or ineffective treatment on covered teeth.

As an alternative, the apparatus could be equipped with a depth-sensing capability in addition to the camera. By combining the data from the camera with depth information, the apparatus can create a more comprehensive understanding of the tooth's structure and position within the oral cavity. This enhanced data fusion technique can further improve the accuracy of determining whether the tooth is exposed or not, leading to more precise and reliable treatment decisions.

Furthermore, the apparatus may offer the flexibility for the user to adjust the sensitivity of the exposure detection feature. This customization option allows the user to set specific thresholds or criteria for what constitutes an exposed tooth based on individual preferences or clinical requirements. By providing this adjustable parameter, the apparatus can cater to a wide range of dental scenarios and ensure optimal performance in diverse clinical settings.

The apparatus, as described above, further may comprise a controller. The controller is configured to cause the apparatus to perform additional operations. These operations include determining if the ligaments that secure the tooth have been cut. The determination is based on a comparison of the captured accelerometer data from the forceps to the predetermined extraction threshold accelerometer data.

Upon a determination that the ligaments have indeed been cut, the controller may also be configured to cause the apparatus to lift out the tooth. The lifting out of the tooth may be achieved with a second elevator, which is part of the at least one elevator.

One such operation may involve determining if the ligaments securing the tooth have been successfully cut. This determination may be made by comparing the accelerometer data captured from the forceps with the predetermined extraction threshold accelerometer data.

Once the controller confirms that the ligaments have been cut, the controller may further direct the apparatus to lift out the tooth. This lifting action may be executed using a second elevator, which is integrated into the at least one elevator present in the apparatus. The second elevator may play a key role in gently extracting the tooth from its socket once the ligaments are confirmed to be severed.

For example, in a dental extraction procedure, the controller may analyze the real-time accelerometer data to assess the status of the tooth's ligaments. If the data indicates that the ligaments have been successfully cut, the controller triggers the second elevator to carefully lift the tooth out of the socket without causing damage to the surrounding tissues. This automated process ensures a smooth and efficient tooth extraction experience for the patient.

An alternative approach could involve incorporating a feedback mechanism into the controller to provide real-time updates on the extraction process. This feedback loop could enable the controller to adjust the lifting force applied by the second elevator based on the resistance encountered during the extraction, ensuring optimal precision and safety during the procedure. Additionally, the controller could be programmed to store data from each extraction, allowing for future analysis and refinement of the extraction technique for improved outcomes.

The apparatus, as described above, may comprise a controller. The controller may be configured to cause the apparatus to perform further operations. These operations may comprise the use of imaging, sensors, and end effectors. The use of these components is in conjunction with computer vision and artificial intelligence (AI) techniques. The purpose of this combination is to evaluate tooth condition and tooth readiness for crown placement.

These images can provide high-resolution data on the tooth structure, allowing the system to analyze the tooth condition accurately.

Additionally, sensors integrated into the apparatus can measure parameters such as temperature, moisture levels, and pressure during the crown placement process. By monitoring these variables in real-time, the controller can ensure optimal conditions for the procedure and make adjustments as needed to enhance the outcome.

Moreover, the end effectors controlled by the apparatus can include robotic arms or precision tools that aid in the placement of dental crowns with high precision and efficiency.

These end effectors can be guided by the controller using AI algorithms to navigate the intricate oral environment and perform the necessary tasks with minimal human intervention.

Furthermore, the integration of computer vision and AI techniques may enable the system to analyze the collected data from imaging and sensors effectively. By leveraging machine learning algorithms, the controller can identify patterns, anomalies, and potential issues related to tooth condition and crown placement readiness, providing valuable insights to the dental practitioner.

For example, the system can detect microfractures or decay in the tooth structure that may impact the success of the crown placement procedure. It can also assess the fit of the crown based on the captured images and sensor data, ensuring a precise and comfortable restoration for the patient.

Alternatively, the controller may incorporate haptic feedback mechanisms to provide tactile information to the dental practitioner during the crown placement process. By simulating the sense of touch, the system can enhance the operator's dexterity and perception, leading to improved outcomes in challenging cases.

The apparatus, as described above, may comprise a controller. The controller is configured to cause the apparatus to perform further operations. These operations comprise evaluating the size and condition of the tooth. In this evaluation, the controller considers factors such as decay, damage, or infection. The controller utilizes probes, sensors, and images as input to an artificial intelligence (AI) system.

The probes can be designed to measure parameters such as tooth density, moisture content, and temperature, providing valuable data for the evaluation process. For example, a probe may be inserted into the tooth to assess the level of decay or damage present.

Additionally, sensors integrated into the apparatus can detect any signs of infection within the tooth. These sensors may be designed to identify specific biomarkers or changes in pH levels that indicate the presence of bacteria or other pathogens. By analyzing this data in conjunction with information from the probes, the controller can generate a comprehensive assessment of the tooth's condition.

Furthermore, the use of images, such as X-rays or intraoral scans, can provide visual information to the AI system. These images can reveal details that may not be apparent from physical measurements alone, allowing the controller to make a more accurate evaluation. For instance, an X-ray image can show the extent of decay within the tooth, while a 3D intraoral scan can provide a detailed view of its structure.

In the apparatus as described above, the controller is further configured to initiate additional operations. These operations comprise assessing the condition of the damaged tooth. Additionally, the controller is configured to determine whether the application of a crown is necessary for the damaged tooth.

If the damage to the tooth is extensive and a traditional filling may not provide adequate support, the controller may recommend the application of a crown to restore the tooth's functionality and appearance. The controller can take into account factors such as the location of the damage, the patient's bite force, and aesthetic considerations when making this determination.

Alternatively, the controller may also consider alternative treatment options to a crown, such as dental implants or bridges, depending on the specific needs of the patient and the condition of the damaged tooth. By evaluating a range of treatment possibilities, the controller can provide personalized recommendations that best suit the individual patient's situation.

The apparatus, as described above, may comprise a controller. The controller is configured to cause the apparatus to perform further operations. These further operations comprise the use of end effectors, such as ablation tools. The purpose of these end effectors is to remove any existing decay. The removal of decay is guided by real-time computer vision. Additionally, the removal process is guided by a three-dimensional digital map of the tooth and the patient's oral cavity. This map is scanned by an imaging sensor.

By utilizing machine learning techniques, the controller can continuously improve its accuracy and efficiency in guiding the end effectors during the decay removal process.

Furthermore, the controller may be programmed to adjust the parameters of the ablation tools based on the specific characteristics of the decay being removed. For example, if the decay is located in a particularly sensitive area of the tooth, the controller can automatically reduce the power or adjust the frequency of the ablation tools to minimize discomfort for the patient.

In an alternative embodiment, the controller could be connected to a cloud-based system that stores vast amounts of data on dental conditions and treatments. By leveraging this data, the controller can provide personalized treatment recommendations based on the patient's unique oral health history and current condition.

In a specific example, the controller could be integrated into a robotic dental system that automates the entire decay removal process. The robotic system, guided by the controller's instructions, can precisely maneuver the end effectors to remove decay with high accuracy and minimal invasiveness.

Additionally, the controller may include a user interface that allows the dentist or dental technician to monitor the progress of the decay removal process in real-time. The interface can display detailed visualizations of the tooth structure, decay removal status, and other relevant information to assist the operator in performing the procedure effectively.

The apparatus, as described above, may comprise a controller. The controller is configured to cause the apparatus to perform further operations. These further operations comprise the removal of tooth material. The removal of tooth material is achieved using one or more end effectors. The purpose of using these one or more end effectors is to shape the tooth. The shaping of the tooth is done in order to accommodate the crown.

For example, harder materials such as enamel may require higher pressure and lower speed for efficient removal, while softer materials such as dentin may require lower pressure and higher speed. This dynamic adjustment ensures precise and efficient shaping of the tooth to accommodate the crown.

Furthermore, the controller may also be equipped with sensors to monitor the progress of tooth material removal in real-time. These sensors can provide feedback on the amount of material removed, the shape of the tooth, and any potential issues such as overheating. Based on this feedback, the controller can automatically adjust the parameters of the end effectors to optimize the shaping process.

Additionally, the controller may have pre-programmed templates for common tooth shapes and crown sizes. This feature allows for quick and easy selection of the desired tooth shape and crown dimensions, streamlining the shaping process. Users can also create custom templates for unique cases, providing flexibility and customization in tooth shaping.

In another embodiment, the apparatus may include multiple sets of end effectors with different shapes and sizes. This allows for versatility in tooth shaping, catering to a wide range of tooth shapes and crown sizes. Users can easily switch between different end effectors based on the specific requirements of the tooth being shaped, enhancing precision and efficiency in the shaping process.

Moreover, the controller may have a learning algorithm that analyzes the shaping patterns and outcomes of previous procedures. By leveraging machine learning, the controller can continuously improve its shaping algorithms and parameters, leading to more accurate and consistent results over time. This adaptive learning capability ensures optimal tooth shaping outcomes with minimal user intervention.

The apparatus, as described above, may comprise a controller. The controller is configured to cause the apparatus to perform further operations. These operations comprise making dental impressions. The dental impressions can be made using either digital scans or traditional molds. The purpose of these scans or molds is to capture the exact shape of the prepared tooth.

This software can provide feedback to the user regarding the quality of the impression, such as whether all necessary details have been captured accurately. For example, the software may highlight areas where the impression is incomplete or where there may be distortions. This real-time feedback can help the user ensure that high-quality impressions are obtained consistently.

Additionally, the controller may be programmed to store a digital record of each dental impression made by the apparatus. These digital records can be accessed and reviewed at a later time, allowing for easy comparison of impressions taken at different times or by different users. This feature can be particularly useful in a dental practice where multiple practitioners may be involved in a patient's treatment, ensuring continuity of care and accurate monitoring of any changes in the patient's dental condition over time.

Furthermore, the controller may have the capability to integrate with other dental software systems, such as patient management software or CAD/CAM systems. This integration can streamline the workflow in a dental practice by allowing for seamless transfer of data between different systems. For example, the controller may automatically populate patient records with the digital impressions taken, eliminating the need for manual data entry and reducing the risk of errors.

In an alternative embodiment, the controller may be equipped with machine learning algorithms that can analyze the digital impressions to identify patterns or anomalies. For instance, the algorithms may be trained to detect early signs of dental issues such as cavities or cracks in the teeth based on the shape and texture of the impressions. This can aid in early diagnosis and treatment planning, potentially improving patient outcomes and reducing the need for invasive procedures in the future.

Moreover, the controller may be designed to allow for remote access, enabling dental professionals to review and analyze the digital impressions from anywhere with an internet connection. This can be particularly beneficial in situations where a specialist consultation is needed or when a practitioner is working in multiple locations. The ability to access and share digital impressions remotely can facilitate collaboration among dental professionals and lead to more comprehensive and efficient treatment planning for patients.

In the apparatus as described above, the controller is further configured to initiate additional operations. These operations comprise directing a three-dimensional milling machine. The direction provided to the milling machine is for the fabrication of the crown. The fabrication process is carried out using a digital model of the patient's oral cavity.

This can involve monitoring parameters such as milling speed, tool wear, material properties, and surface finish quality. By continuously adjusting these parameters during the fabrication process, the controller can ensure the final crown meets the desired specifications with high precision and efficiency.

For example, the controller may adjust the milling speed based on the hardness of the material being milled to prevent tool wear or overheating. It can also dynamically change the tool path to optimize the surface finish quality of the crown. Additionally, the controller can detect any deviations between the digital model and the actual milling process and make real-time corrections to ensure the final crown matches the intended design accurately.

Furthermore, the controller can be equipped with machine learning algorithms to analyze data from previous milling processes and continuously improve the fabrication techniques. By learning from past experiences, the controller can anticipate potential issues and proactively adjust the milling parameters to prevent errors or defects in the final crown.

The apparatus, as described above, may comprise a controller. The controller is configured to cause the apparatus to perform further operations. These further operations comprise interactively collaborating with the milling machine and the human dentist. The interactive collaboration is facilitated via a high-resolution touch-screen interactive display. The high-resolution touch-screen interactive display is used to guide the crown preparation. The guidance for the crown preparation is provided using a digital map of the patient's oral cavity. The digital map of the patient's oral cavity is scanned by a camera.

These algorithms can provide suggestions and feedback to the human dentist during the crown preparation process. For example, the AI algorithms may detect areas that require more precision or adjustments and highlight them on the high-resolution touch-screen interactive display for the dentist's attention.

Additionally, the controller may be programmed to store data from each crown preparation procedure. This data can include details such as the specific tools used, the duration of the procedure, and any deviations from the initial plan. By analyzing this data over time, the controller can provide insights to the human dentist on ways to improve efficiency and accuracy in future procedures.

As an alternative embodiment, the high-resolution touch-screen interactive display could be replaced with a virtual reality (VR) headset. The VR headset can provide an immersive 3D visualization of the patient's oral cavity, allowing the dentist to have a more detailed and realistic view during the crown preparation. This alternative setup can offer a unique perspective and potentially improve the precision of the procedure.

The apparatus, as described above, further may comprise a controller. The controller may be configured to cause the apparatus to perform additional operations. These operations may involve the iterative removal of tooth material. The purpose of this iterative removal is to resize the tooth stump or post. The resized tooth stump or post may be prepared to accept the crown while the crown is being milled by the milling machine.

The controller may operate in a communication and control feedback loop. This feedback loop may compare the size of the stump or post, which is measured by an optical scan, to a digital model. The digital model may represent the interior of the crown.

The controller can take into account factors such as the desired dimensions of the final crown, the material properties of the tooth stump or post, and the capabilities of the milling machine. By dynamically adjusting the removal parameters based on real-time feedback from the optical scan, the controller ensures that the resizing process is accurate and efficient.

For example, if the optical scan indicates that the tooth stump or post is slightly larger than the digital model of the crown, the controller may instruct the apparatus to remove a smaller amount of material in the next iteration. Conversely, if the scan reveals that more material needs to be removed for a proper fit, the controller can adjust the cutting parameters accordingly. This iterative approach allows for precise customization of the crown preparation process to achieve optimal results.

Furthermore, the controller may incorporate machine learning capabilities to continuously improve the resizing process over time. By analyzing data from previous resizing procedures and outcomes, the controller can identify patterns and trends to enhance its decision-making process. This adaptive learning mechanism may enable the controller to refine its algorithms and strategies, leading to increased accuracy and efficiency in resizing tooth stumps or posts for crown placement.

In the apparatus as described above, the controller may be further configured to initiate additional operations. These operations may comprise the placement of the crown onto the tooth. The crown is affixed to the tooth using either cement or a suitable dental adhesive.

The robotic arm can be controlled with high precision to ensure accurate placement of the crown. The gripper may be designed to securely hold the crown during the placement process, preventing any accidental displacement.

Alternatively, the apparatus may include a computer vision system that utilizes cameras and image processing algorithms to guide the placement of the crown onto the tooth. The cameras may capture real-time images of the tooth and the crown, allowing the system to analyze the position and orientation of the crown relative to the tooth. Based on this analysis, the controller can adjust the position of the crown as needed to ensure proper alignment before affixing it to the tooth.

In another variation, the apparatus may incorporate a pressure sensor in the gripper or at the tip of the robotic arm. The pressure sensor can detect the amount of force applied during the placement of the crown onto the tooth. This feature enables the controller to monitor and control the pressure exerted on the crown, ensuring gentle and precise placement without causing any damage to the tooth or the crown.

In the Summary above and in this Detailed Description, and the Claims below, and in the accompanying drawings, reference is made to particular features of various implementations. It is to be understood that the disclosure of particular features of various implementations in this specification is to be interpreted to include all possible combinations of such particular features. For example, where a particular feature is disclosed in the context of a particular aspect or implementation, or a particular claim, that feature can also be used—to the extent possible—in combination with and/or in the context of other particular aspects and implementations, and in an implementation generally.

While multiple implementations are disclosed, still other implementations will become apparent to those skilled in the art from this detailed description. Disclosed implementations may be capable of myriad modifications in various obvious aspects, all without departing from the spirit and scope of the disclosed implementations. Accordingly, the drawings and descriptions are to be regarded as illustrative in nature and not restrictive.

It should be noted that the features illustrated in the drawings are not necessarily drawn to scale, and features of one implementation may be employed with other implementations as the skilled artisan would recognize, even if not explicitly stated herein. Descriptions of well-known components and processing techniques may be omitted so as to not unnecessarily obscure the implementation features.

In the present disclosure, various features may be described as being optional, for example, through the use of the verb "may;" or, through the use of any of the phrases: "in some implementations," "in some designs," "in various implementations," "in various designs," "in an illustrative example," or, "for example." For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be implemented in seven different ways, namely with just one of the three possible features, with any two of the three possible features or with all three of the three possible features.

In various implementations, elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various implementations have been disclosed and described in detail herein, it will be apparent to those skilled in the art that various changes may be made to the disclosed configuration, operation, and form without departing from the spirit and scope thereof. In particular, it is noted that the respective implementation features, even those disclosed solely in combination with other implementation features, may be combined in any configuration excepting those readily apparent to the person skilled in the art as nonsensical. Likewise, use of the singular and plural is solely for the sake of illustration and is not to be interpreted as limiting.

The Abstract is provided to comply with 37 C. F. R. § 1.72(b), to allow the reader to quickly ascertain the nature of the technical disclosure and is submitted with the understanding that it will not be used to interpret or limit the scope or meaning of the claims.

In the present disclosure, any method or apparatus implementation may be devoid of one or more process steps or components. In the present disclosure, implementations employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an implementation "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose limit is the second number. For example, 25 to 100 mm means a range whose lower limit is 25 mm and upper limit is 100 mm.

Many suitable methods and corresponding materials to make each of the individual parts of implementation apparatus are known in the art. One or more implementation part may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described hereinabove may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112(f). Specifically, any use of "step of" in the claims herein is not intended to invoke the provisions of 35 U.S.C. § 112(f). Elements recited in means-plus-function format are intended to be construed in accordance with 35 U.S.C. § 112(f).

Recitation in a claim of the term "first" with respect to a feature or element does not necessarily imply the existence of a second or additional such feature or element.

The phrases "connected to," "coupled to" and "in communication with" refer to any form of interaction between two or more entities, including mechanical, electrical, chemical, magnetic, electromagnetic, fluid, and thermal interaction. Two components may be functionally coupled to each other even though they are not in direct contact with each other. The terms "abutting" or "in mechanical union" refer to items that are in direct physical contact with each other, although the items may not necessarily be attached together.

The word "exemplary" is used herein to mean "serving as an example, instance, or illustration." Any implementation described herein as "exemplary" is not necessarily to be construed as preferred over other implementations. While various aspects of the disclosure are presented with reference to drawings, the drawings are not necessarily drawn to scale unless specifically indicated.

Reference throughout this specification to "an implementation" or "the implementation" means that a particular feature, structure, or characteristic described in connection with that implementation is included in at least one implementation. Thus, the quoted phrases, or variations thereof, as recited throughout this specification are not necessarily all referring to the same implementation.

Similarly, it should be appreciated that in the above description, various features are sometimes grouped together in a single implementation, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects may lie in a combination of fewer than all features of any single foregoing disclosed implementation. Thus, the claims following this Detailed Description are hereby expressly incorporated into this Detailed Description, with each claim standing on its own as a separate implementation. This disclosure is intended to be interpreted as including all permutations of the independent claims with their dependent claims.

A system or method implementation in accordance with the present disclosure may be accomplished through the use of one or more computing devices. As depicted, for example, at least in FIG. 1 and FIG. 2, one of ordinary skill in the art would appreciate that an exemplary system appropriate for use with implementation in accordance with the present application may generally include one or more of a Central processing Unit (CPU), Random Access Memory (RAM), a storage medium (e.g., hard disk drive, solid state drive, flash memory, cloud storage), an operating system (OS), one or more application software, a display element, one or more communications means, or one or more input/output devices/means. Examples of computing devices usable with implementations of the present disclosure include, but are not limited to, proprietary computing devices, personal computers, mobile computing devices, tablet PCs, mini-PCs, servers, or any combination thereof. The term computing device may also describe two or more computing devices communicatively linked in a manner as to distribute and share one or more resources, such as clustered computing devices and server banks/farms. One of ordinary skill in the art would understand that any number of computing devices could be used, and implementation of the present disclosure are contemplated for use with any computing device.

As used in this application, the terms "component," "environment," "system," "architecture," "interface," "unit," "module," "pipe," and the like are intended to refer to a computer-related entity or an entity related to an operational apparatus with one or more specific functionalities. Such entities may be either hardware, a combination of hardware and software, software, or software in execution. As an example, a component may be, but is not limited to being, a process running on a processor, a processor, an object, an executable portion of software, a thread of execution, a program, and/or a computing device. For example, both a software application executing on a computing device containing a processor circuit and the computing device may be a component. One or more components may reside within a process and/or thread of execution. A component may be localized on one computing device or distributed between two or more computing devices. As described herein, a component may execute from various computer-readable non-transitory media having various data structures stored thereon. Components may communicate via local and/or remote processes in accordance, for example, with one or more signals (for example, analog and/or digital) having one or more data packets (e.g., data from one component interacting with another component in a local system, distributed system, and/or across a network such as a wide area network with other systems via the signal). As another example, a component may be an apparatus with specific functionality provided by mechanical parts operated by electric or electronic circuitry that is controlled by a software application or firmware application executed by a processor circuit, wherein the processor may be internal or external to the apparatus and may execute at least a part of the software or firmware application. As another example, a component may be an apparatus that provides specific functionality through electronic components without mechanical parts, and the electronic components may include a processor therein to execute software or firmware that provides, at least in part, the functionality of the electronic components. In certain embodiments, components may communicate via local and/or remote processes in accordance, for example, with a signal having one or more data packets (e.g., data from one component interacting with another component in a local system, distributed system, and/or across a network such as a wide area network with other systems via the signal). In other embodiments, components may communicate or otherwise be coupled via thermal, mechanical, electrical, and/or electromechanical coupling mechanisms (such as conduits, connectors, combinations thereof, or the like). An interface may include input/output (I/O) components as well as associated processors, applications, and/or other programming components. The terms "component," "environment," "system," "architecture," "interface," "unit," "module," and "pipe" may be utilized interchangeably and may be referred to collectively as functional elements.

As utilized in this disclosure, the term "processor" may refer to any computing processing unit or device comprising single-core processors; single processors with software multithread execution capability; multi-core processors; multi-core processors with software multithread execution capability; multi-core processors with hardware multithread technology; parallel platforms; and parallel platforms with distributed shared memory. Additionally, a processor may refer to an integrated circuit (IC), an application-specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. A processor may be implemented as a combination of computing processing units. In certain embodiments, processors may utilize nanoscale architectures such as, but not limited to, molecular and quantum-dot based transistors, switches, and gates, to optimize space usage or enhance the performance of user equipment or other electronic equipment.

As used herein, a singular term may include multiple objects. As used herein, a single element may include multiple such elements. For example, the term "computer" may include a single computer or multiple computers. The phrase "a computer that stores data and runs software," may include a single computer that both stores data and runs software, a first computer that stores data and a second computer that runs software, or multiple computers that together store data and run software, where at least one of the multiple computers stores data and at least one of the multiple computers runs software. For example, the term "processor" may include a single processor or multiple processors. The phrase "a processor that stores data and runs software," may include a single processor that both stores data and runs software, a first processor that stores data and a second processor that runs software, or multiple processors that together store data and run software, where at least one of the multiple processors stores data and at least one of the multiple processors runs software. An implementation comprising multiple processors may configure each particular processor of the multiple processors to exclusively execute only a particular task assigned to that particular processor. An implementation comprising multiple processors may configure each particular processor of the multiple processors to execute any task of multiple tasks assigned to that particular processor by a scheduler such that a different task may be assigned to different processors at different times. As used herein in an apparatus or a computer-readable medium, "at least one" object rather than or in addition to a single object may perform the claimed operations. For example, "a computer-readable medium" may be construed as "at least one computer-readable medium," and "an apparatus comprising a processor and a memory" may be construed as "a system comprising processing circuitry and a memory subsystem," or "a system comprising processing circuitry and memory" (where memory lacks the article 'a'). It should be noted that a skilled person would understand that "processing circuitry" may include a single processor or multiple processors. Similarly "memory subsystem" or "memory" (lacking an article) may include a single memory unit or multiple memory units.

In addition, in the present specification and annexed drawings, terms such as "store," "storage," "data store," "data storage," "memory," "repository," and substantially any other information storage component relevant to the operation and functionality of a component of the disclosure, refer to "memory components," entities embodied in a "memory," or components forming the memory. It may be appreciated that the memory components or memories described herein embody or comprise non-transitory computer storage media that may be readable or otherwise accessible by a computing device. Such media may be implemented in any methods or technology for storage of information such as computer-readable instructions, information structures, program modules, or other information objects. The memory components or memories may be either volatile memory or non-volatile memory, or may include both volatile and non-volatile memory. In addition, the memory components or memories may be removable or non-removable, and/or internal or external to a computing device or component. Examples of various types of non-transitory storage media may include hard-disc drives, zip drives, CD-ROMs, digital versatile disks (DVDs) or other optical storage, magnetic cassettes, magnetic tape, magnetic disk storage or other magnetic storage devices, flash memory cards or other types of memory cards, cartridges, or any other non-transitory medium suitable to retain the desired information and which may be accessed by a computing device.

In various implementations, communications means, data store(s), processor(s), or memory may interact with other components on the computing device, in order to effect the provisioning and display of various functionalities associated with the system and method detailed herein. One of ordinary skill in the art would appreciate that there are numerous configurations that could be utilized with implementations of the present disclosure, and implementations of the present disclosure are contemplated for use with any appropriate configuration.

According to an implementation of the present disclosure, the communications means of the system may be, for instance, any means for communicating data over one or more networks or to one or more peripheral devices attached to the system. Appropriate communications means may include, but are not limited to, circuitry and control systems for providing wireless connections, wired connections, cellular connections, data port connections, Bluetooth® connections, or any combination thereof. One of ordinary skill in the art would appreciate that there are numerous communications means that may be utilized with implementations of the present disclosure, and implementations of the present disclosure are contemplated for use with any communications means.

Throughout this disclosure and elsewhere, block diagrams and flowchart illustrations depict methods, apparatuses (i.e., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general purpose hardware and computer instructions; and so on-any and all of which may be generally referred to herein as a "circuit," "module," or "system."

While the foregoing drawings and description may set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an implementation may include an alternate order of the steps adapted to a particular application of a technique disclosed herein. All such variations and modifications are intended to fall within the scope of this disclosure. The depiction and description of steps in any particular order is not intended to exclude implementations having the steps in a different order, unless required by a particular application, explicitly stated, or otherwise clear from the context.

Traditionally, a computer program consists of a sequence of computational instructions or program instructions. It will be appreciated that a programmable apparatus (that is, computing device) can receive such a computer program and, by processing the computational instructions thereof, produce a further technical effect.

A programmable apparatus may include one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computer can include any and all suitable combinations of at least one general purpose computer, special-purpose computer, programmable data processing apparatus, processor, processor architecture, and so on.

It will be understood that a computer can include a computer-readable storage medium and that this medium may be internal or external, removable, and replaceable, or fixed. It will also be understood that a computer can include a Basic Input/Output System (BIOS), firmware, an operating system, a database, or the like that can include, interface with, or support the software and hardware described herein.

Implementations of the system as described herein are not limited to applications involving conventional computer programs or programmable apparatuses that run them. It is contemplated, for example, that implementations of the disclosure as claimed herein could include an optical computer, quantum computer, analog computer, or the like.

Regardless of the type of computer program or computer involved, a computer program can be loaded onto a computer to produce a particular machine that can perform any and all of the depicted functions. This particular machine provides a means for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. A computer readable storage medium may be a non-transitory computer readable storage medium. A non-transitory computer readable storage medium may be a computer readable storage medium that is not a transitory propagating signal. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code encoded therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code encoded by a computer readable medium may be transmitted using any appropriate medium, including but not limited to wireless, wireline, optical fiber cable, RF, etc., or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software modules, or as modules that employ external routines, code, services, and so forth, or any combination of these. All such implementations are within the scope of the present disclosure.

Unless explicitly stated or otherwise clear from the context, the verbs "execute" and "process" are used interchangeably to indicate execute, process, interpret, compile, assemble, link, load, any and all combinations of the foregoing, or the like. Therefore, implementations that execute or process computer program instructions, computer-executable code, or the like can suitably act upon the instructions or code in any and all of the ways just described.

The functions and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, implementations of the disclosure are not described with reference to any particular programming language. It is appreciated that a variety of programming languages may be used to implement the present teachings as described herein, and any references to specific languages are provided for disclosure of enablement and best mode of implementations of the disclosure. Implementations of the disclosure are well suited to a wide variety of computer network systems over numerous topologies. Within this field, the configuration and management of large networks include storage devices and computers that are communicatively coupled to dissimilar computers and storage devices over a network, such as the Internet.

A number of implementations have been described. Nevertheless, it will be understood that various modifications may be made. For example, the steps of the disclosed techniques may be performed in a different sequence, components of the disclosed systems may be combined in a different manner, or the components may be supplemented with other components. Accordingly, other implementations are contemplated, within the scope of the following claims.

What is claimed is:

1. A method comprising:
   receiving a scanned image of a tooth and a surrounding area, using at least one processor;
   presenting the scanned image of the tooth to a dentist, using the at least one processor and a user interface; and
   upon receiving, from the dentist via the user interface, confirmation that a correct tooth is targeted for extraction:
      determining if the tooth is decayed based on analysis of the scanned image of the tooth by a trained decay classification machine learning model, using the at least one processor;
      in response to determining the tooth is not decayed:
         grabbing a neck of the tooth, using the at least one processor and forceps;
      in response to determining the tooth is decayed:
         presenting the scanned image of the tooth to the dentist using the at least one processor and the user interface;
         determining if the tooth is completely decayed based on analysis of the scanned image of the tooth by a trained decay extent determination machine learning model, using the at least one processor;
         in response to determining the tooth is completely decayed:
            receiving an extraction plan created by the dentist for the completely decayed tooth, using the at least one processor and the user interface, wherein the extraction plan comprises sectioning roots of the completely decayed tooth; and
            sectioning the roots of the completely decayed tooth, using the at least one processor and a surgical handpiece; and
         in response to determining the tooth is not completely decayed:
            presenting the scanned image of the tooth to the dentist using the at least one processor and the user interface, for identifying a firm surface location on the tooth; and in response to receiving identification of a firm surface location on the tooth, grabbing a neck of the tooth at the firm surface location on the tooth, using the at least one processor and forceps;

severing a periodontal ligament and luxating the tooth, using the at least one processor and an elevator/luxator; and extracting the tooth, using the at least one processor and the forceps.

2. The method of claim 1, wherein after extracting the tooth, the method further comprises receiving a scanned image of the area surrounding the extracted tooth, using the at least one processor.

3. The method of claim 2, wherein the method further comprises determining if there is bleeding from the area surrounding the extracted tooth, based on analysis of the scanned image, using the at least one processor.

4. The method of claim 2, wherein the method further comprises in response to determining there is bleeding, stopping the bleeding, using the at least one processor and a laser.

5. The method of claim 1, wherein the method further comprises injecting an anesthetic, using the at least one processor and a syringe.

6. The method of claim 5, wherein the anesthetic further comprises Novocaine®.

7. The method of claim 1, wherein receiving the scanned image further comprises receiving an image resulting from an optical scan, an X-ray or a CT scan.

8. The method of claim 1, wherein the method further comprises presenting the scanned image depicting the tooth to the dentist with an indication that an image-based object detection algorithm has determined the depicted tooth is the correct tooth targeted for extraction.

9. The method of claim 1, wherein the trained decay classification machine learning model further comprises at least one Convolutional Neural Network (CNN).

10. The method of claim 9, wherein the at least one CNN is trained with a training data set comprising labeled ground truth images depicting decayed or healthy teeth.

11. The method of claim 9, and wherein the at least one CNN is trained to classify an image of the tooth as depicting at least some decay or no decay determined as a function of an input image.

12. The method of claim 1, wherein the trained decay extent determination machine learning model further comprises at least one Convolutional Neural Network (CNN) trained with a training data set comprising ground truth images subdivided into a mesh of cell regions.

13. The method of claim 12, wherein the ground truth images are labeled as decayed or healthy.

14. The method of claim 12, wherein each ground truth image of an individual tooth is labeled with a percentage value of grid cells which show decayed tooth material for the individual tooth.

15. The method of claim 12, wherein the decay extent determination machine learning model is trained to determine a percentage of grid cells showing decayed tooth material as a function of an input image.

16. The method of claim 1, wherein the method further comprises selecting surface locations that are not decayed on opposing sides of the tooth, by the at least one processor using the trained decay extent determination machine learning model.

17. The method of claim 16, wherein the method further comprises applying gripping force to the selecting surface locations, using the at least one processor.

18. The method of claim 1, wherein the method further comprises determining if a patient is bleeding from an extraction site based on comparing color histograms of images of the extraction site before extraction and after extraction.

19. The method of claim 1, wherein the method further comprises determining if a patient is bleeding from an extraction site based on an optical flow algorithm analyzing a video of the extraction site captured after extraction.

20. An article of manufacture comprising a non-transitory computer readable storage medium retrievably storing processor executable instructions configured to cause a robotic dentistry system to perform tooth extraction operations comprising:

receive a scanned image of a tooth and a surrounding area, using at least one processor;

present the scanned image of the tooth to a dentist, using the at least one processor and a user interface;

upon receiving confirmation from the dentist via the user interface that the tooth targeted for extraction is correct:

determine if the tooth is decayed based on analysis of the scanned image of the tooth by a trained decay classification machine learning model, using the at least one processor;

in response to determining the tooth is not decayed, grab a neck of the tooth, using the at least one processor and forceps;

in response to determining the tooth is decayed, grab a surface of the tooth above the neck of the tooth, using the at least one processor and the forceps;

sever a periodontal ligament and luxate the tooth, using the at least one processor and an elevator/luxator; and extract the tooth, using the at least one processor and the forceps.

* * * * *